United States Patent
Donde et al.

(10) Patent No.: US 9,394,273 B2
(45) Date of Patent: Jul. 19, 2016

(54) THERAPEUTIC PROSTAGLANDIN RECEPTOR AGONISTS

(71) Applicant: Allergan, Inc., Irvine, CA (US)

(72) Inventors: Yariv Donde, Dana Point, CA (US); Jeremiah H. Nguyen, La Puente, CA (US)

(73) Assignee: ALLERGAN, INC., Irvine, CA (US)

( * ) Notice: Subject to any disclaimer, the term of this patent is extended or adjusted under 35 U.S.C. 154(b) by 0 days.

(21) Appl. No.: 14/712,105

(22) Filed: May 14, 2015

(65) Prior Publication Data

US 2015/0329518 A1   Nov. 19, 2015

Related U.S. Application Data

(60) Provisional application No. 61/994,018, filed on May 15, 2014.

(51) Int. Cl.

| | |
|---|---|
| *C07D 333/62* | (2006.01) |
| *C07C 405/00* | (2006.01) |
| *C07D 319/18* | (2006.01) |
| *C07D 333/54* | (2006.01) |
| *A61K 8/49* | (2006.01) |
| *A61Q 7/00* | (2006.01) |
| *C07C 63/66* | (2006.01) |
| *C07D 333/56* | (2006.01) |
| *C07D 319/16* | (2006.01) |
| *A61K 8/368* | (2006.01) |
| *C07D 333/60* | (2006.01) |

(52) U.S. Cl.
CPC .............. *C07D 333/62* (2013.01); *A61K 8/368* (2013.01); *A61K 8/498* (2013.01); *A61K 8/4986* (2013.01); *A61Q 7/00* (2013.01); *C07C 63/66* (2013.01); *C07C 405/00* (2013.01); *C07D 319/16* (2013.01); *C07D 319/18* (2013.01); *C07D 333/54* (2013.01); *C07D 333/56* (2013.01); *C07D 333/60* (2013.01); *C07C 2101/08* (2013.01)

(58) Field of Classification Search
CPC .. C07D 333/62; C07D 333/60; C07D 319/18; C07D 333/54; C07D 333/56; C07D 319/16; C07C 405/00; C07C 63/66; C07C 2101/08; A61K 8/498; A61K 8/368; A61K 8/4986; A61Q 7/00
See application file for complete search history.

(56) References Cited

U.S. PATENT DOCUMENTS

| | | | |
|---|---|---|---|
| 4,166,452 | A | 9/1979 | Generales, Jr. |
| 4,256,108 | A | 3/1981 | Theeuwes |
| 4,265,874 | A | 5/1981 | Bonsen et al. |
| 2014/0142042 | A1 | 5/2014 | Jiang et al. |

FOREIGN PATENT DOCUMENTS

| | | | | |
|---|---|---|---|---|
| JP | WO 0166518 A1 | * | 9/2001 | ........ C07C 405/0016 |
| WO | 9519964 | | 7/1995 | |
| WO | 2006113571 | | 10/2006 | |

OTHER PUBLICATIONS

Stahl, P.H., et al., Handbook of Pharmaceutical Salts, Properties, Selection, and Use, 2002, 329-345.
Johnson, Carl R., et al., A Two-Step, Three-Component Synthesis of PGE1: Utilization of a-Iodoenones in Pd (0)-Catalyzed Cross-Couplings of Organoboranes, JACS 1993, 115: 11014-11015.
Remington's Pharmaceutical Sciences, 1980, 16th edition, pp. 1-10.
Silverman, Richard, Prodrugs and Drug Delivery Systems, Organic Chemistry of Drug Design and Drug Action 2nd edition, 2004, 496-557.
Notification of Transmittal of the International Search Report and Written Opinion mailed on Aug. 3, 2015 for PCT/US2015/031163 filed May 15, 2015 in the name of Allergan, Inc.

* cited by examiner

*Primary Examiner* — Samantha Shterengarts
*Assistant Examiner* — Matt Mauro
(74) *Attorney, Agent, or Firm* — Jonathan Bass

(57) ABSTRACT

Described herein are compounds which can be used in topical liquids, creams, or other dosage forms such as solids, for reducing intraocular pressure, treating glaucoma, growing hair, treating wounds, or other medical and/or cosmetic uses.

27 Claims, No Drawings

THERAPEUTIC PROSTAGLANDIN RECEPTOR AGONISTS

CROSS-REFERENCE TO RELATED APPLICATIONS

This application claims the benefit of U.S. Provisional Application Ser. No. 61/994,018, filed on May 15, 2014, which is incorporated herein by reference in its entirety.

FIELD

The present disclosure is drawn towards compounds, compositions, and methods of treating various conditions, and in particular therapeutic prostaglandin receptor agonists which in some embodiments are useful for the treatment of conditions such as glaucoma and wounds and for promoting hair growth and reducing intraocular pressure.

BACKGROUND

Ocular hypotensive agents are useful in the treatment of a number of various ocular hypertensive conditions, such as post-surgical and post-laser trabeculectomy ocular hypertensive episodes, glaucoma, and as pre-surgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, prostaglandin analogs are the current first line treatment for glaucoma management.

BRIEF SUMMARY

Described herein are optionally substituted cyclopentanones, such as optionally substituted 2,3-diarylalkyl cyclopentanones, which can have binding or activity at prostaglandin receptors, such as prostaglandin E receptors, including EP4. These compounds may be useful in treating diseases or conditions such as elevated intraocular pressure, glaucoma, hair loss, etc.

Some embodiments include a compound represented by Formula 1:

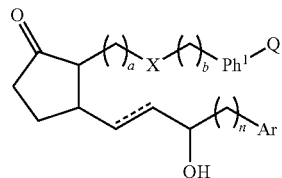

Formula 1 or a pharmaceutically acceptable salt thereof, wherein a dashed line indicates the presence or absence of a double bond; Q is $CO_2R^1$, $CH_2OR^1$, $CONR^1R^2$, or optionally substituted tetrazol-5-yl, wherein $R^1$ and $R^2$ are independently H, $C_{1-6}$ alkyl, $C_{1-6}$ hydroxyalkyl, morpholinoethyl, or optionally substituted phenyl; $Ph^1$ is optionally substituted interphenylene; a and b are independently 0, 1, or 2; X is $CH_2$, O, or S; n is 0, 1, or 2; and Ar is optionally substituted aryl or optionally substituted heteroaryl.

Some embodiments include an ophthalmic liquid comprising a compound described herein and one or more pharmaceutically acceptable excipients.

Some embodiments include a solid dosage form comprising a compound described herein more non-toxic solid carriers.

Some embodiments include a method of reducing intraocular pressure, or treating glaucoma, comprising administering a compound described herein, or a pharmaceutically acceptable salt thereof, to an eye of a mammal in need thereof.

Some embodiments include a method of growing hair comprising administering a compound described herein, or a pharmaceutically acceptable salt thereof, to a mammal in which hair growth is desirable, e.g. to an area of the mammal where hair growth is desired.

Some embodiments include a method of healing a wound comprising administering a compound described herein, or a pharmaceutically acceptable salt thereof, to a mammal in need thereof. In some embodiments, administration of a compound described herein may be useful for the healing of dermal or epithelial wounds, including for example wounds relating to cosmetic surgery.

DETAILED DESCRIPTION

Certain eicosanoids and their derivatives can be used in glaucoma management. Eicosanoids and derivatives include numerous biologically important compounds such as prostaglandins and their derivatives. Prostaglandins can be described as derivatives of prostanoic acid. Prostanoic acid has the following structural formula:

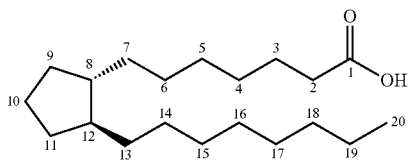

Various types of prostaglandins are classified by the structure and substituents carried on the alicyclic ring of the prostanoic acid skeleton. Further classification is based on the number of unsaturated bonds in the side chain indicated by numerical subscripts after the generic type of prostaglandin [e.g. prostaglandin E$_1$ (PGE$_1$), prostaglandin E$_2$ (PGE$_2$)], and on the configuration of the substituents on the alicyclic ring indicated by α or β [e.g. prostaglandin F$_{2α}$ (PGF$_{2α}$)]. Changes in the substituents of carbons 9, 10, and 11 can often influence the activity and selectivity of these compounds at the different prostaglandin receptors. Other compounds having more remote structures from natural prostaglandins can also have activity at prostaglandin receptors. For example, some optionally substituted 2,3-diarylalkyl cyclopentanones can have activity at prostaglandin receptors, such as the prostaglandin EP$_4$ receptor.

Unless otherwise indicated, when a compound or chemical structural feature such as aryl is referred to as being "optionally substituted," it includes a feature that has no substituents (i.e. unsubstituted), or a feature that is "substituted," meaning that the feature has one or more substituents. The term "substituent" has the broadest meaning known to one of ordinary skill in the art, and includes a moiety that replaces one or more hydrogen atoms in a parent compound or structural feature. The term "replaces" is merely used herein for convenience, and does not require that the compound be formed by replacing one atom with another. In some embodiments, a substituent may be any ordinary organic moiety known in the art, which may have a molecular weight (e.g. the sum of the atomic masses of the atoms of the substituent) of 15 g/mol to 50 g/mol, 15 g/mol to 100 g/mol, 15 g/mol to 150 g/mol, 15 g/mol to 200 g/mol, 15 g/mol to 300 g/mol, or 15 g/mol to 500 g/mol. In some embodiments, a substituent comprises, or consists of: 0-30, 0-20, 0-10, or 0-5 carbon atoms; and 0-30, 0-20, 0-10, or 0-5 heteroatoms, wherein each heteroatom may independently be: N, O, P, S, Si, F, Cl, Br, or I; provided that the substituent includes one C, N, O, P, S, Si, F, Cl, Br, or I atom.

Where substituents are specified as a range, the range encompasses each individual integer value of substituent including the beginning and ending value of the range. For example, the description of a substituent as "C$_1$ to C$_6$ alkyl" (or "C$_1$-C$_6$ alkyl" or "C$_{1-6}$ alkyl") encompasses C$_1$ alkyl, C$_2$ alkyl, C$_3$ alkyl, C$_4$ alkyl, C$_6$ alkyl, and C$_6$ alkyl. Similarly, the description of a value of "n" (e.g. "(CH$_2$)$_n$") as being "0 to 3" (or "0-3") encompasses values of "n" of 0, 1, 2, and 3. A skilled person will realize upon a reading of the present disclosure that similar considerations apply to other substituents that can be described in terms of a range (e.g. "5 to 10 ring atoms" and "1 to 3 rings").

Examples of substituents include, but are not limited to, hydrocarbyl, such as alkyl, alkenyl, alkynyl; heteroalkyl, including any moiety wherein one or more heteroatoms replaces one or more carbon atoms of an alkyl moiety, and some accompanying hydrogen atoms (e.g. N replaces CH, O replaces CH$_2$, Cl replaces CH$_3$, etc.), such as alkoxy, alkylthio, haloalkyl, haloalkoxy, amino, etc.; heteroalkenyl, including any moiety wherein one or more heteroatoms replaces one or more carbon atoms of an alkenyl moiety, and some accompanying hydrogen atoms, such as acyl, acyloxy, thiocarbonyl, al kylcarboxylate, O-carbamyl, N-carbamyl, O-thiocarbamyl, N-thiocarbamyl, C-amido, N-amido, sulfinyl, isocyanato, isothiocyanato, etc; heteroalkynyl, including any moiety wherein one or more heteroatoms replaces one or more carbon atoms of an alkynyl moiety, and some accompanying hydrogen atoms, such as cyano, thiocyanato, cyanato; aryl; heteroaryl; hydroxy; aryloxy; thiol; halo; S-sulfonamido; N-sulfonamido; nitro, silyl; sulfonyl; trihalomethanesulfonyl; trihalomethanesulfonamido; etc.

For convenience, the term "molecular weight" is used with respect to a moiety or part of a molecule to indicate the sum of the atomic masses of the atoms in the moiety or part of a molecule, even though it may not be a complete molecule.

The structures associated with some of the chemical names referred to herein are depicted below. These structures may be unsubstituted, as shown below, or a substituent may independently be in any position normally occupied by a hydrogen atom when the structure is unsubstituted. Unless a point of attachment is indicated by ―│, attachment may occur at any position normally occupied by a hydrogen atom.

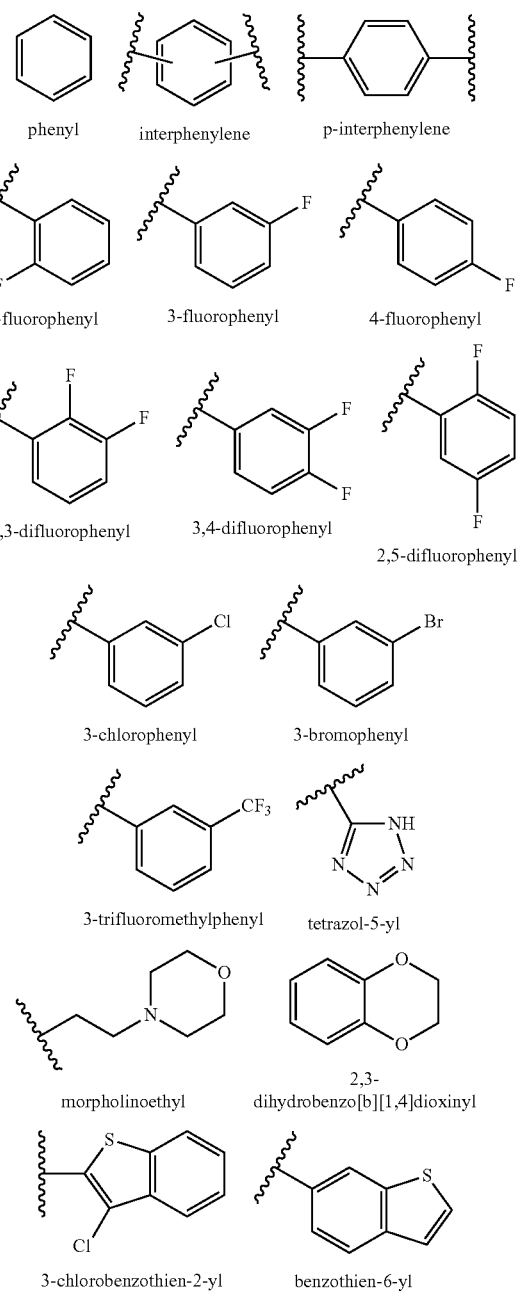

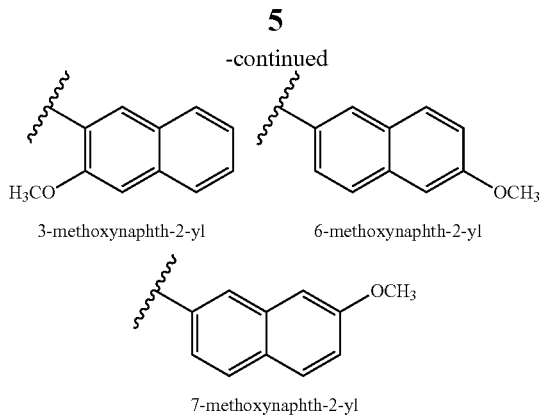

3-methoxynaphth-2-yl     6-methoxynaphth-2-yl 7-methoxynaphth-2-yl

As used herein, the term "alkyl" has the broadest meaning generally understood in the art, and may include a moiety composed of carbon and hydrogen containing no double or triple bonds. Alkyl may be linear alkyl, branched alkyl, cycloalkyl, or a combination thereof, and in some embodiments, may contain from one to thirty-five carbon atoms. In some embodiments, alkyl may include $C_{1-10}$ linear alkyl, such as methyl (—$CH_3$), ethyl (—$CH_2CH_3$), n-propyl (—$CH_2CH_2CH_3$), n-butyl (—$CH_2CH_2CH_2CH_3$), n-pentyl (—$CH_2CH_2CH_2CH_2CH_3$), n-hexyl (—$CH_2CH_2CH_2CH_2CH_2CH_3$), etc.; $C_{3-10}$ branched alkyl, such as $C_3H_7$ (e.g. iso-propyl), $C_4H_9$ (e.g. branched butyl isomers), $C_5H_{11}$ (e.g. branched pentyl isomers), $C_6H_{13}$ (e.g. branched hexyl isomers), $C_7H_{15}$ (e.g. branched heptyl isomers), etc.; $C_{3-10}$ cycloalkyl, such as $C_3H_5$ (e.g. cyclopropyl), $C_4H_7$ (e.g. cyclobutyl isomers such as cyclobutyl, methylcyclopropyl, etc.), $C_5H_9$ (e.g. cyclopentyl isomers such as cyclopentyl, methylcyclobutyl, dimethylcyclopropyl, etc.) $C_6H_{11}$ (e.g. cyclohexyl isomers), $C_7H_{13}$ (e.g. cycloheptyl isomers), etc.; and the like.

As used herein, the term "hydroxyalkyl" has the broadest meaning generally understood in the art, and includes alkyl having one or more hydroxyl substituents, such as $CH_2OH$, $CH_2CH_2OH$, $C_3H_6OH$, etc.

As used herein the term "aryl" has the broadest meaning generally understood in the art, and includes a ring or a ring system having at least one aromatic ring, such as phenyl, naphthyl, 2,3-dihydrobenzo[b][1,4]dioxinyl, etc.

The term "heteroarylene" also has the meaning understood by a person of ordinary skill in the art, and includes an aryl which has one or more heteroatoms in the ring or ring system, such as pyridinyl, furyl, thienyl, interoxazolylene, thiazolyl, imidazolyl, quinolinyl, benzofuryl, benzothienyl, etc.

Unless otherwise indicated, any reference to a compound herein by structure, name, or any other means, includes pharmaceutically acceptable salts, such as sodium, potassium, and ammonium salts; prodrugs, such as ester prodrugs; alternate solid forms, such as polymorphs, solvates, hydrates, etc.; tautomers; or any other chemical species that may rapidly convert to a compound described herein under conditions in which the compounds are used as described herein.

If stereochemistry is not indicated, such as in Formulas 2-4, a name or structural depiction includes any stereoisomer or any mixture of stereoisomers.

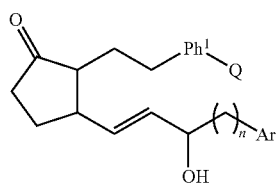

Formula 2

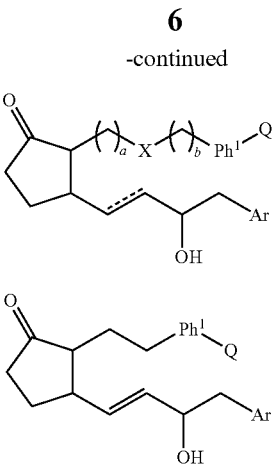

Formula 3

Formula 4

With respect to any relevant structural representation, such as Formula 1 or 3, a dashed line indicates the presence or absence of a double bond. Thus, as illustrated with respect to Formula 1 or 3, the dashed line can be absent resulting in a single bond, as shown in Formulas 1a and 3a, or the dashed line can be present resulting in a double bond, as shown in Formulas 1b, and 3b.

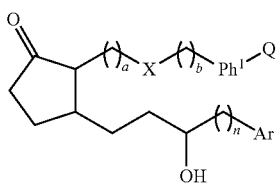

Formula 1a

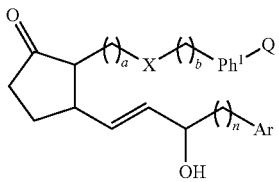

Formula 1b

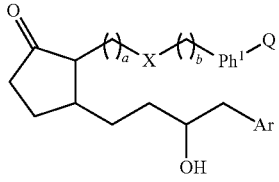

Formula 3a

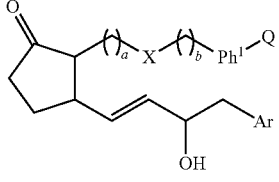

Formula 3b

With respect to any relevant structural representation, such as Formula 1, 1a, 1b 2, 3, 3a, 3b, or 4, Q is $CO_2R^1$, $CH_2OR^1$, $CONR^1R^2$, or optionally substituted tetrazol-5-yl.

$R^1$ is H, $C_{1-6}$ alkyl, $C_{1-6}$ hydroxyalkyl, morpholinoethyl, or optionally substituted phenyl. In some embodiments, $R^1$ is H, $C_{1-6}$ alkyl, such as $CH_3$, $C_2H_5$, $C_3H_7$, $C_4H_9$, etc.

$R^2$ is H, $C_{1-6}$ alkyl, $C_{1-6}$ hydroxyalkyl, morpholinoethyl, or optionally substituted phenyl. In some embodiments, $R^2$ is H.

With respect to any relevant structural representation, such as Formula 1, 1a, 1b, 3, 3a, or 3b, a is 0, 1, or 2. In some embodiments, a is 1.

With respect to any relevant structural representation, such as Formula 1, 1a, 1b, 3, 3a, or 3b, b is 0, 1, or 2. In some embodiments, b is 0.

With respect to any relevant structural representation, such as Formula 1, 1a, 1b, 3, 3a, or 3b, X is $CH_2$, O, or S. In some embodiments, X is $CH_2$.

With respect to Formula 1, 1a, 1b, 3, 3a, or 3b, in some embodiments a is 1, b is 0, and X is $CH_2$.

With respect to any relevant structural representation, such as Formula 1, 1a, 1b, or 2, n is 0, 1, or 2. In some embodiments, n is 1.

With respect to any relevant structural representation, such as Formula 1, 1a, 1b, 2, 3, 3a, 3b, or 4, in some embodiments, Q is $CO_2R^1$, such as $CO_2H$, $CO_2CH_3$, $CO_2CH_2CH_3$, $CO_2CH(CH_3)_2$, $CO_2CH_2CH_2OH$,

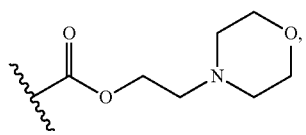 [SMILES: *C(=O)OCCN1CCOCC1]

etc.

With respect to any relevant structural representation, such as Formula 1, 1a, 1b, 2, 3, 3a, 3b, or 4, $Ph^1$ is optionally substituted interphenylene, such as optionally substituted p-interphenylene, optionally substituted o-interphenylene, or optionally substituted m-interphenylene. In some embodiments, $Ph^1$ is unsubstituted. If $Ph^1$ is substituted, it may have 1, 2, 3, or 4 substituents. In some embodiments, some or all of the substituents on $Ph^1$ may have: from 0 to 10 carbon atoms and from 0 to 10 heteroatoms, wherein each heteroatom is independently: O, N, P, S, F, Cl, Br, or I (provided that there is at least 1 non-hydrogen atom); and/or a molecular weight of 15 g/mol to 150 g/mol, 300 g/mol, or 500 g/mol. For example, the substituents may be $C_{1-20}$ alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc.; $C_{1-20}$ alkoxyl; $C_{1-20}$ hydroxyalkyl; halo, such as F, Cl, Br, or I; OH; CN; $NO_2$; $C_{1-6}$ fluoroalkyl, such as $CF_3$, $CF_2H$, $C_2F_5$, etc.; a $C_{1-10}$ ester such as $-O_2CCH_3$, $-CO_2CH_3$, $-O_2CC_2H_5$, $-CO_2C_2H_5$, $-O_2C$-phenyl, $-CO_2$-phenyl, etc.; a $C_{1-10}$ ketone such as $-COCH_3$, $-COC_2H_5$, $-COC_3H_7$, $-CO$-phenyl, etc.; or a $C_{1-10}$ amino such as $NH_2$, $NH(CH_3)$, $N(CH_3)_2$, $N(CH_3)C_2H_5$, etc. In some embodiments, $Ph^1$ is unsubstituted, or any substituents are F, Cl, Br, $CH_3$, $OCH_3$, $NH_2$, or $CF_3$. In some embodiments, in Formula 1, 1a, 1b, 2, 3, 3a, 3b, or 4, $Ph^1$ is an optionally substituted p-interphenylene, such as a p-interphenylene of Formula A:

(Formula A)

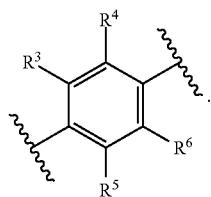

With respect to Formula A, $R^3$, $R^4$, $R^5$, and $R^6$ may independently be H or any substituent, such as a substituent having from 0 to 6 carbon atoms and from 0 to 5 heteroatoms, wherein each heteroatom is independently: O, N, P, S, F, Cl, Br, or I; and/or having a molecular weight of 15 g/mol to 300 g/mol, or 15 g/mol to 150 g/mol. In some embodiments, $R^3$, $R^4$, $R^5$, and $R^6$ are independently $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^3$, $R^4$, $R^5$, and $R^6$ are independently H; F; Cl; CN; $CF_3$; OH; $NH_2$; $C_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc.

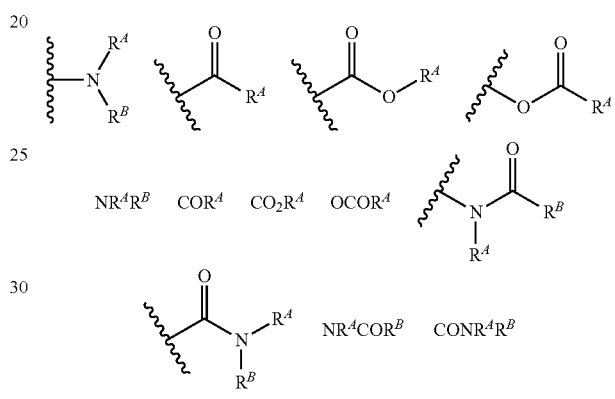

$NR^AR^B$    $COR^A$    $CO_2R^A$    $OCOR^A$ $NR^ACOR^B$    $CONR^AR^B$

With respect to any relevant structural representation, each $R^A$ may independently be H, or $C_{1-12}$ alkyl, including: linear or branched alkyl having a formula $C_aH_{2a+1}$, or cycloalkyl having a formula $C_aH_{2a-1}$, wherein a is 1, 2, 3, 4, 5, 6, 7, 8, 9, 10, 11, or 12, such as linear or branched alkyl of a formula: $CH_3$, $C_2H_5$, $C_3H_7$, $C_4H_9$, $C_5H_{11}$, $C_6H_{13}$, $C_7H_{15}$, $C_8H_{17}$, $C_9H_{19}$, $C_{10}H_{21}$, etc., or cycloalkyl of a formula: $C_3H_5$, $C_4H_7$, $C_5H_9$, $C_6H_{11}$, $C_7H_{13}$, $C_8H_{15}$, $C_9H_{17}$, $C_{10}H_{19}$, etc. In some embodiments, $R^A$ may be H or $C_{1-6}$ alkyl. In some embodiments, $R^A$ may be H or $C_{1-3}$ alkyl. In some embodiments, $R^A$ may be H or $CH_3$. In some embodiments, $R^A$ may be H.

With respect to any relevant structural representation, each $R^B$ may independently be H, or $C_{1-12}$ alkyl, including: linear or branched alkyl having a formula $C_aH_{2a+1}$; or cycloalkyl having a formula $C_aH_{2a-1}$, wherein a is 1, 2, 3, 4, 5, 6, 7, 8, 9, 10, 11, or 12, such as linear or branched alkyl of a formula: $CH_3$, $C_2H_5$, $C_3H_7$, $C_4H_9$, $C_5H_{11}$, $C_6H_{13}$, $C_8H_{17}$, $C_7H_{15}$, $C_9H_{19}$, $C_{10}H_{21}$, etc., or cycloalkyl of a formula: $C_3H_5$, $C_4H_7$, $C_5H_9$, $C_6H_{11}$, $C_7H_{13}$, $C_8H_{15}$, $C_9H_{17}$, $C_{10}H_{19}$, etc. In some embodiments, $R^B$ may be H or $C_{1-3}$ alkyl. In some embodiments, $R^B$ may be H or $CH_3$. In some embodiments, $R^B$ may be H.

With respect to Formula A, in some embodiments, $R^3$ is H, F, Cl, or $CH_3$. In some embodiments, $R^3$ is H. Additionally, for any embodiments recited in this paragraph, $R^4$, $R^5$, and $R^6$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to Formula A, in some embodiments, $R^4$ is H, F, Cl, or $CH_3$. In some embodiments, $R^4$ is H. Additionally, for any embodiments recited in this paragraph, $R^3$, $R^5$, and $R^6$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to Formula A, in some embodiments, $R^5$ is H, F, Cl, or $CH_3$. In some embodiments, $R^5$ is H. Additionally, for any embodiments recited in this paragraph, $R^3$, $R^4$, and $R^6$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to Formula A, in some embodiments, $R^6$ is H, F, Cl, or $CH_3$. In some embodiments, $R^6$ is H. Additionally, for any embodiments recited in this paragraph, $R^3$, $R^4$, and $R^5$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to Formula A, in some embodiments, $R^3$ and $R^4$ are H. In some embodiments, $R^3$ and $R^5$ are H. In some embodiments, $R^3$ and $R^6$ are H. In some embodiments, $R^3$, $R^4$, $R^5$, and $R^6$ are H.

With respect to any relevant structural representation, such as Formula 1, 1a, 1b, 2, 3, 3a, 3b, or 4, Ar is optionally substituted aryl or optionally substituted heteroaryl. In some embodiments, Ar is optionally substituted phenyl, optionally substituted 2,3-dihydrobenzo[b][1,4]dioxinyl, optionally substituted benzothienyl, or optionally substituted naphthyl. If Ar is optionally substituted phenyl, it may have 0, 1, 2, 3, 4, or 5 substituents. If Ar is optionally substituted naphthyl or optionally substituted dihydrobenzo[b][1,4]dioxinyl, it may have 0, 1, 2, 3, 4, 5, 6, or 7 substituents. If Ar is, optionally substituted benzothienyl, it may have 0, 1, 2, 3, or 4 substituents. Ar may have any substituent. In some embodiments, some or all of the substituents of Ar may have: from 0 to 10 carbon atoms and from 0 to 10 heteroatoms, wherein each heteroatom is independently: O, N, P, S, F, Cl, Br, or I (provided that there is at least 1 non-hydrogen atom); and/or a molecular weight of 15 g/mol to 100 g/mol, 200 g/mol, or 500 g/mol. For example, the substituents may be $C_{1-20}$ alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc.; $C_{1-20}$ alkoxyl; $C_{1-20}$ hydroxyalkyl; halo, such as F, Cl, Br, I; OH; CN; $NO_2$; $C_{1-6}$ fluoroalkyl, such as $CF_3$, $CF_2H$, $C_2F_5$, etc.; a $C_{1-10}$ ester such as $—O_2CCH_3$, $—CO_2CH_3$, $—O_2CC_2H_5$, $—CO_2C_2H_5$, $—O_2C—$phenyl, $—CO_2$-phenyl, etc.; a $C_{1-10}$ ketone such as $—COCH_3$, $—COC_2H_5$, $—COC_3H_7$, $—CO—$phenyl, etc.; or a $C_{1-10}$ amino such as $NH_2$, $NH(CH_3)$, $N(CH_3)_2$, $N(CH_3)$ $C_2H_5$, etc. In some embodiments a substituent of Ar is F, Cl, Br, $CF_3$, or $OCH_3$.

With respect to any relevant structural representation, such as Formula 1, 1a, 1b, 2, 3, 3a, 3b, or 4, in some embodiments, Ar is a fluorophenyl, such as 2-fluorophenyl, 3-fluorophenyl, 4-fluorophenyl, 2,3-difluorophenyl, 3,4-difluorophenyl, 2,5-difluorophenyl; a chlorophenyl, such as 3-chlorophenyl; a bromophenyl, such as 3-bromophenyl; or a trifluoromethylphenyl, such as 3-trifluoromethylphenyl. In some embodiments, Ar is:

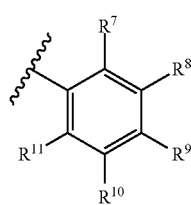

(Formula B)

With respect to any relevant structural representation, such as Formula B, $R^7$, $R^8$, $R^9$, $R^{10}$ and $R^{11}$ may independently be H or any substituent, such as a substituent having from 0 to 6 carbon atoms and from 0 to 5 heteroatoms, wherein each heteroatom is independently: O, N, P, S, F, Cl, Br, or I, and/or having a molecular weight of 15 g/mol to 300 g/mol, or 15 g/mol to 150 g/mol. In some embodiments, $R^7$, $R^8$, $R^9$, and $R^{10}$ are independently $R^A$, F, Cl, Br, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^7$, $R^8$, $R^9$, $R^{10}$ and $R^{11}$ are independently H; F; Cl; CN; $CF_3$; OH; $NH_2$; $C_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc.

With respect to Formula B, in some embodiments at least one of $R^7$, $R^8$, $R^9$, $R^{10}$ and $R^{11}$ is not H. In some embodiments, $R^7$ is not H. In some embodiments, $R^8$ is not H. In some embodiments, $R^9$ is not H. In some embodiments, $R^{10}$ is not H.

With respect to any relevant structural representation, such as Formula B, in some embodiments $R^7$ is H, F, Cl, $C_{1-10}$ alkyl, or $C_{1-10}$ hydroxyalkyl. In some embodiments $R^7$ is H or F. In some embodiments, $R^7$ is H. In some embodiments, $R^7$ is F. Additionally, for any embodiments recited in this paragraph, $R^8$, $R^9$, $R^{10}$, and $R^{11}$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to any relevant structural representation, such as Formula B, in some embodiments $R^8$ is H, F, Cl, $C_{1-10}$ alkyl, or $C_{1-10}$ hydroxyalkyl. In some embodiments, $R^8$ is H, F, Cl, Br, or $CF_3$. In some embodiments, $R^8$ is H. In some embodiments, $R^8$ is F. In some embodiments, $R^8$ is Cl. In some embodiments, $R^8$ is Br. In some embodiments, $R^8$ is $CF_3$. Additionally, for any embodiments recited in this paragraph, $R^7$, $R^9$, $R^{10}$, and $R^{11}$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to any relevant structural representation, such as Formula B, in some embodiments $R^7$ is F and $R^8$ is F.

With respect to any relevant structural representation, such as Formula B, in some embodiments $R^9$ is H, F, Cl, $C_{1-10}$ alkyl, or $C_{1-10}$ hydroxyalkyl. In some embodiments, $R^9$ is H or F. In some embodiments, $R^9$ is H. In some embodiments, $R^9$ is F. Additionally, for any embodiments recited in this paragraph, $R^7$, $R^8$, $R^{10}$, and $R^{11}$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to any relevant structural representation, such as Formula B, in some embodiments $R^8$ is F and $R^9$ is F.

With respect to any relevant structural representation, such as Formula B, in some embodiments $R^{10}$ is H, F, Cl, $C_{1-10}$ alkyl, or $C_{1-10}$ hydroxyalkyl. In some embodiments, $R^{10}$ is H or F. In some embodiments, $R^{10}$ is H. In some embodiments, $R^{10}$ is F. Additionally, for any embodiments recited in this paragraph, $R^7$, $R^8$, $R^9$, and $R^{11}$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to any relevant structural representation, such as Formula B, in some embodiments $R^7$ is F and $R^{10}$ is F.

With respect to any relevant structural representation, such as Formula B, in some embodiments $R^{11}$ is H, F, Cl, $C_{1-10}$ alkyl, or $C_{1-10}$ hydroxyalkyl. In some embodiments, $R^{11}$ is H. Additionally, for any embodiments recited in this paragraph, $R^7$, $R^8$, $R^9$, and $R^{10}$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to any relevant structural representation, such as Formula 1, 1a, 1b, 2, 3, 3a, 3b, or 4, in some embodiments, Ar is optionally substituted 2,3-dihydrobenzo[b][1,4]dioxinyl, such as unsubstituted 2,3-dihydrobenzo[b][1,4]dioxinyl. In some embodiments, Ar is:

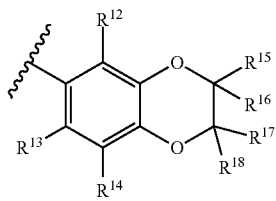

(Formula C)

With respect to any relevant structural representation, such as Formula C, $R^{12}$, $R^{13}$, $R^{14}$, $R^{15}$, $R^{16}$, $R^{17}$, and $R^{18}$ may independently be H or any substituent, such as a substituent having from 0 to 6 carbon atoms and from 0 to 5 heteroatoms, wherein each heteroatom is independently: O, N, P, S, F, Cl, Br, or I, and/or having a molecular weight of 15 g/mol to 300 g/mol, or 15 g/mol to 150 g/mol. In some embodiments, $R^7$, $R^8$, $R^9$, and $R^{10}$ are independently $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^7$, $R^8$, $R^9$, $R^{10}$ and $R^{11}$ are independently H; F; Cl; CN; $CF_3$; OH; $NH_2$; $C_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc.

With respect to any relevant structural representation, such as Formula C, in some embodiments $R^{12}$ is H, F, Cl, $C_{1-10}$ alkyl, or $C_{1-10}$ hydroxyalkyl. In some embodiments, $R^{12}$ is H. Additionally, for any embodiments recited in this paragraph, $R^{13}$, $R^{14}$, $R^{15}$, $R^{16}$, $R^{17}$, and $R^{18}$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to any relevant structural representation, such as Formula C, in some embodiments $R^{13}$ is H, F, Cl, $C_{1-10}$ alkyl, or $C_{1-10}$ hydroxyalkyl. In some embodiments, $R^{13}$ is H. Additionally, for any embodiments recited in this paragraph, $R^{12}$, $R^{14}$, $R^{15}$, $R^{16}$, $R^{17}$, and $R^{18}$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to any relevant structural representation, such as Formula C, in some embodiments $R^{14}$ is H, F, Cl, $C_{1-10}$ alkyl, or $C_{1-10}$ hydroxyalkyl. In some embodiments, $R^{14}$ is H. Additionally, for any embodiments recited in this paragraph, $R^{12}$, $R^{13}$, $R^{15}$, $R^{16}$, $R^{17}$, and $R^{18}$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to any relevant structural representation, such as Formula C, in some embodiments $R^{12}$, $R^{13}$, and $R^{14}$ are H.

With respect to any relevant structural representation, such as Formula C, in some embodiments $R^{15}$ is H, F, Cl, $C_{1-10}$ alkyl, or $C_{1-10}$ hydroxyalkyl. In some embodiments, $R^{15}$ is H. Additionally, for any embodiments recited in this paragraph, $R^{12}$, $R^{13}$, $R^{14}$, $R^{15}$, $R^{16}$, $R^{17}$, and $R^{18}$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to any relevant structural representation, such as Formula C, in some embodiments $R^{16}$ is H, F, Cl, $C_{1-10}$ alkyl, or $C_{1-10}$ hydroxyalkyl. In some embodiments, $R^{16}$ is H. Additionally, for any embodiments recited in this paragraph, $R^{12}$, $R^{13}$, $R^{14}$, $R^{15}$, $R^{17}$, and $R^{18}$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to any relevant structural representation, such as Formula C, in some embodiments $R^{17}$ is H, F, Cl, $C_{1-10}$ alkyl, or $C_{1-10}$ hydroxyalkyl. In some embodiments, $R^{17}$ is H. Additionally, for any embodiments recited in this paragraph, $R^{12}$, $R^{13}$, $R^{14}$, $R^{15}$, $R^{16}$, and $R^{18}$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to any relevant structural representation, such as Formula C, in some embodiments $R^{18}$ is H, F, Cl, $C_{1-10}$ alkyl, or $C_{1-10}$ hydroxyalkyl. In some embodiments, $R^{18}$ is H. Additionally, for any embodiments recited in this paragraph, $R^{12}$, $R^{13}$, $R^{14}$, $R^{15}$, $R^{16}$, and $R^{17}$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to any relevant structural representation, such as Formula C, in some embodiments $R^{15}$, $R^{16}$, $R^{17}$, and $R^{18}$ are H.

With respect to any relevant structural representation, such as Formula 1, 1a, 1b, 2, 3, 3a, 3b, or 4, in some embodiments, Ar is a chlorobenzothien-2-yl, such as a 3-chlorobenzothien-2-yl; or an unsubstituted benzothienyl, such as benzothien-6-yl.

In some embodiments, Ar is:

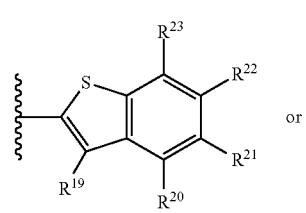

(Formula D)

or

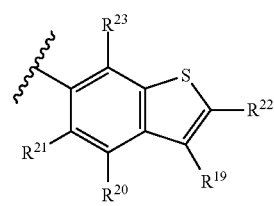

(Formula E)

With respect to any relevant structural representation, such as Formula D or E, $R^{19}$, $R^{20}$, $R^{21}$, $R^{22}$, and $R^{23}$ may independently be H or any substituent, such as a substituent having from 0 to 6 carbon atoms and from 0 to 5 heteroatoms, wherein each heteroatom is independently: O, N, P, S, F, Cl, Br, or I, and/or having a molecular weight of 15 g/mol to 300 g/mol, or 15 g/mol to 150 g/mol. In some embodiments, $R^{19}$, $R^{20}$, $R^{21}$, $R^{22}$, and $R^{23}$ are independently $R^A$, F, Cl, Br, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{19}$, $R^{20}$, $R^{21}$, $R^{22}$, and $R^{23}$ are independently H; F; Cl; CN; $CF_3$; OH; $NH_2$; $C_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; or $C_{1-6}$ alkoxy, such as —O-methyl, —O— ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc.

With respect to any relevant structural representation, such as Formula D or E, in some embodiments $R^{19}$ is H, F, Cl, $C_{1-10}$ alkyl, or $C_{1-10}$ hydroxyalkyl. In some embodiments, $R^{19}$ is H or Cl. In some embodiments, $R^{19}$ is H. In some embodiments, $R^{19}$ is Cl. Additionally, for any embodiments recited in this paragraph, $R^{20}$, $R^{21}$, $R^{22}$, and $R^{23}$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to any relevant structural representation, such as Formula D or E, in some embodiments $R^{20}$ is H, F, Cl, $C_{1-10}$ alkyl, or $C_{1-10}$ hydroxyalkyl. In some embodiments, $R^{20}$ is H. Additionally, for any embodiments recited in this paragraph, $R^{19}$, $R^{21}$, $R^{22}$, and $R^{23}$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to any relevant structural representation, such as Formula D or E, in some embodiments $R^{21}$ is H, F, Cl, $C_{1-10}$ alkyl, or $C_{1-10}$ hydroxyalkyl. In some embodiments, $R^{21}$ is H. Additionally, for any embodiments recited in this paragraph, $R^{19}$, $R^{20}$, $R^{22}$, and $R^{23}$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to any relevant structural representation, such as Formula D or E, in some embodiments $R^{22}$ is H, F, Cl, $C_{1-10}$ alkyl, or $C_{1-10}$ hydroxyalkyl. In some embodiments, $R^{22}$ is H. Additionally, for any embodiments recited in this paragraph, $R^{19}$, $R^{20}$, $R^{21}$, and $R^{23}$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to any relevant structural representation, such as Formula D or E, in some embodiments $R^{23}$ is H, F, Cl, $C_{1-10}$ alkyl, or $C_{1-10}$ hydroxyalkyl. In some embodiments, $R^{23}$ is H. Additionally, for any embodiments recited in this paragraph, $R^{19}$, $R^{20}$, $R^{21}$, and $R^{22}$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to any relevant structural representation, such as Formula 1, 1a, 1b, 2, 3, 3a, 3b, or 4, in some embodiments, Ar is optionally substituted naphthyl, such as unsubstituted naphth-2-yl; or a methoxynaphthyl, such as 3-methoxynaphth-2-yl, 6-methoxynaphth-2-yl, or 7-methoxynaphth-2-yl. In some embodiments, Ar is:

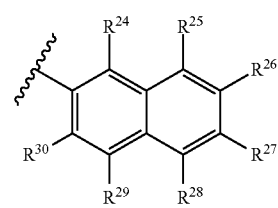

(Formula F)

With respect to any relevant structural representation, such as Formula F, $R^{24}$, $R^{25}$, $R^{26}$, $R^{27}$, $R^{28}$, $R^{29}$, and $R^{30}$ may independently be H or any substituent, such as a substituent having from 0 to 6 carbon atoms and from 0 to 5 heteroatoms, wherein each heteroatom is independently: O, N, P, S, F, Cl, Br, or I, and/or having a molecular weight of 15 g/mol to 300 g/mol, or 15 g/mol to 150 g/mol. In some embodiments, $R^{19}$, $R^{20}$, $R^{21}$, $R^{22}$, and $R^{23}$ are independently $R^A$, F, Cl, Br, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{19}$, $R^{20}$, $R^{21}$, $R^{22}$, and $R^{23}$ are independently H; F; Cl; CN; $CF_3$; OH; $NH_2$; $C_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; or $C_{1-6}$ alkoxy, such as —O-methyl, —O— ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc.

With respect to any relevant structural representation, such as Formula F, in some embodiments $R^{24}$ is H, F, Cl, $C_{1-10}$ alkyl, or $C_{1-10}$ hydroxyalkyl. In some embodiments, $R^{24}$ is H. Additionally, for any embodiments recited in this paragraph, $R^{25}$, $R^{26}$, $R^{27}$, $R^{28}$, $R^{29}$, and $R^{30}$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to any relevant structural representation, such as Formula F, in some embodiments $R^{25}$ is H, F, Cl, $C_{1-10}$ alkyl, or $C_{1-10}$ hydroxyalkyl. In some embodiments, $R^{25}$ is H. Additionally, for any embodiments recited in this paragraph, $R^{24}$, $R^{26}$, $R^{27}$, $R^{28}$, $R^{29}$, and $R^{30}$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to any relevant structural representation, such as Formula F, in some embodiments $R^{26}$ is H, F, Cl, $C_{1-10}$ alkyl, or $C_{1-10}$ hydroxyalkyl. In some embodiments, $R^{26}$ is H or $OCH_3$. In some embodiments, $R^{26}$ is H. In some embodiments, $R^{26}$ is $OCH_3$. Additionally, for any embodiments recited in this paragraph, $R^{24}$, $R^{25}$, $R^{27}$, $R^{28}$, $R^{29}$, and $R^{30}$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to any relevant structural representation, such as Formula F, in some embodiments $R^{27}$ is H, F, Cl, $C_{1-10}$ alkyl, or $C_{1-10}$ hydroxyalkyl. In some embodiments, $R^{27}$ is H or $OCH_3$. In some embodiments, $R^{27}$ is H. In some embodiments, $R^{27}$ is $OCH_3$. Additionally, for any embodiments recited in this paragraph, $R^{24}$, $R^{25}$, $R^{26}$, $R^{28}$, $R^{29}$, and $R^{30}$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to any relevant structural representation, such as Formula F, in some embodiments $R^{28}$ is H, F, Cl, $C_{1-10}$ alkyl, or $C_{1-10}$ hydroxyalkyl. In some embodiments, $R^{28}$ is H. Additionally, for any embodiments recited in this paragraph, $R^{24}$, $R^{25}$, $R^{26}$, $R^{27}$, $R^{29}$, and $R^{30}$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to any relevant structural representation, such as Formula F, in some embodiments $R^{29}$ is H, F, Cl, $C_{1-10}$ alkyl, or $C_{1-10}$ hydroxyalkyl. In some embodiments, $R^{29}$ is H. Additionally, for any embodiments recited in this paragraph, $R^{24}$, $R^{25}$, $R^{26}$, $R^{27}$, $R^{28}$, and $R^{30}$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to any relevant structural representation, such as Formula F, in some embodiments $R^{30}$ is H, F, Cl, $C_{1-10}$ alkyl, or $C_{1-10}$ hydroxyalkyl. In some embodiments, $R^{30}$ is H or $OCH_3$. In some embodiments, $R^{30}$ is H. In some embodiments, $R^{30}$ is $OCH_3$. Additionally, for any embodiments recited in this paragraph, $R^{24}$, $R^{25}$, $R^{26}$, $R^{27}$, $R^{28}$, and $R^{29}$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

Some embodiments include optionally substituted (E)-4-(2-(2-(3-hydroxy-4-(naphthalen-2-yl)but-1-en-1-yl)-5-oxocyclopentyl)ethyl)benzoic acid; optionally substituted (E)-4-(2-(2-(4-(3-chlorobenzo[b]thiophen-2-yl)-3-hydroxybut-1-en-1-yl)-5-oxocyclopentyl)ethyl)benzoic acid; optionally substituted (E)-4-(2-(2-(4-(3-fluorophenyl)-3-hydroxybut-1-en-1-yl)-5-oxocyclopentyl)ethyl)benzoic acid; optionally substituted (E)-4-(2-(2-(4-(3-chlorophenyl)-3-hydroxybut-1-en-1-yl)-5-oxocyclopentyl)ethyl)benzoic acid; optionally substituted (E)-4-(2-(2-(4-(3-bromophenyl)-3-hydroxybut-1-en-1-yl)-5-oxocyclopentyl)ethyl)benzoic acid; optionally substituted (E)-4-(2-(2-(3-hydroxy-4-(3-(trifluoromethyl)phenyl)but-1-en-1-yl)-5-oxocyclopentyl)ethyl)benzoic acid; optionally substituted (E)-4-(2-(2-(3-hydroxy-4-(7-methoxy-2,3-dihydrobenzo[b][1,4]dioxin-6-yl)but-1-en-1-yl)-5-oxocyclopentyl)ethyl)benzoic acid; optionally substituted (E)-4-(2-(2-(4-(benzo[b]thiophen-6-yl)-3-hydroxybut-1-en-1-yl)-5-oxocyclopentyl)ethyl)benzoic acid; optionally substituted (E)-4-(2-(2-(3-hydroxy-4-(6-methoxynaphthalen-2-yl)but-1-en-1-yl)-5-oxocyclopentyl)ethyl)benzoic acid; optionally substituted (E)-4-(2-(2-(3-hydroxy-4-(3-methoxynaphthalen-2-yl)but-1-en-1-yl)-5-oxocyclopentyl)ethyl) benzoic acid; optionally substituted (E)-4-(2-(2-(3-hydroxy-4-(7-methoxynaphthalen-2-yl)but-1-en-1-yl)-5-oxocyclopentyl)ethyl)benzoic acid; optionally substituted (E)-4-(2-(2-(4-(4-fluorophenyl)-3-hydroxybut-1-en-1-yl)-5-oxocyclopentyl)ethyl)benzoic acid; optionally substituted (E)-4-(2-(2-(4-(2-fluorophenyl)-3-hydroxybut-1-en-1-yl)-5-oxocyclopentyl)ethyl)benzoic acid; optionally substituted (E)-4-(2-(2-(4-(3,4-difluorophenyl)-3-hydroxybut-1-en-1-yl)-5-oxocyclopentyl)ethyl)benzoic acid; optionally substituted (E)-4-(2-(2-(4-(2,3-difluorophenyl)-3-hydroxybut-1-en-1-yl)-5-oxocyclopentyl)ethyl)benzoic acid; or optionally substituted (E)-4-(2-(2-(4-(2,5-difluorophenyl)-3-hydroxybut-1-en-1-yl)-5-oxocyclopentyl)ethyl)benzoic acid.

Some embodiments include (E)-4-(2-(2-(3-hydroxy-4-(naphthalen-2-yl)but-1-en-1-yl)-5-oxocyclopentyl)ethyl) benzoic acid; (E)-4-(2-(2-(4-(3-chlorobenzo[b]thiophen-2-yl)-3-hydroxybut-1-en-1-yl)-5-oxocyclopentyl)ethyl) benzoic acid; (E)-4-(2-(2-(4-(3-fluorophenyl)-3-hydroxybut-1-en-1-yl)-5-oxocyclopentyl)ethyl)benzoic acid; (E)-4-(2-(2-(4-(3-chlorophenyl)-3-hydroxybut-1-en-1-yl)-5-oxocyclopentyl)ethyl)benzoic acid; (E)-4-(2-(2-(4-(3-bromophenyl)-3-hydroxybut-1-en-1-yl)-5-oxocyclopentyl) ethyl)benzoic acid; (E)-4-(2-(2-(3-hydroxy-4-(3-(trifluoromethyl)phenyl)but-1-en-1-yl)-5-oxocyclopentyl) ethyl)benzoic acid; (E)-4-(2-(2-(3-hydroxy-4-(7-methoxy-2,3-dihydrobenzo[b][1,4]dioxin-6-yl)but-1-en-1-yl)-5-oxocyclopentyl)ethyl)benzoic acid; (E)-4-(2-(2-(4-(benzo[b]thiophen-6-yl)-3-hydroxybut-1-en-1-yl)-5-oxocyclopentyl) ethyl)benzoic acid; (E)-4-(2-(2-(3-hydroxy-4-(6-methoxynaphthalen-2-yl)but-1-en-1-yl)-5-oxocyclopentyl) ethyl)benzoic acid; (E)-4-(2-(2-(3-hydroxy-4-(3-methoxynaphthalen-2-yl)but-1-en-1-yl)-5-oxocyclopentyl) ethyl)benzoic acid; (E)-4-(2-(2-(3-hydroxy-4-(7-methoxynaphthalen-2-yl)but-1-en-1-yl)-5-oxocyclopentyl) ethyl)benzoic acid; (E)-4-(2-(2-(4-(4-fluorophenyl)-3-hydroxybut-1-en-1-yl)-5-oxocyclopentyl)ethyl)benzoic acid; (E)-4-(2-(2-(4-(2-fluorophenyl)-3-hydroxybut-1-en-1-yl)-5-oxocyclopentyl)ethyl)benzoic acid; (E)-4-(2-(2-(4-(3,4-difluorophenyl)-3-hydroxybut-1-en-1-yl)-5-oxocyclopentyl)ethyl)benzoic acid; (E)-4-(2-(2-(4-(2,3-difluorophenyl)-3-hydroxybut-1-en-1-yl)-5-oxocyclopentyl)ethyl)benzoic acid; or (E)-4-(2-(2-(4-(2,5-difluorophenyl)-3-hydroxybut-1-en-1-yl)-5-oxocyclopentyl)ethyl)benzoic acid.

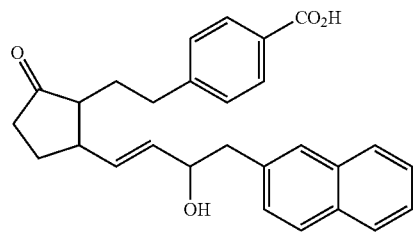

(E)-4-(2-(2-(3-hydroxy-4-(naphthalen-2-yl)but-1-en-1-yl)-5-oxocyclopentyl)ethyl)benzoic acid

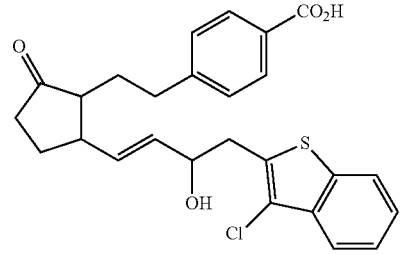

(E)-4-(2-(2-(4-(3-chlorobenzo[b]thiophen-2-yl)-3-hydroxybut-1-en-1-yl)-5-oxocyclopentyl)ethyl) benzoic acid

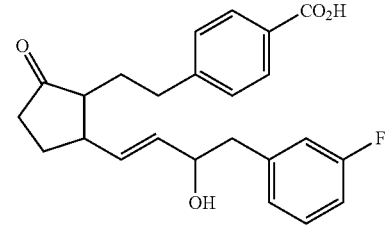

(E)-4-(2-(2-(4-(3-fluorophenyl)-3-hydroxybut-1-en-1-yl)-5-oxocyclopentyl)ethyl)benzoic acid

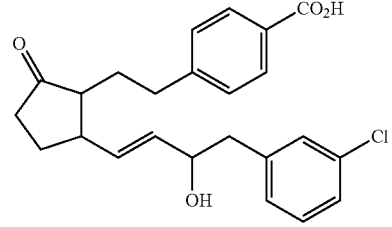

(E)-4-(2-(2-(4-(3-chlorophenyl)-3-hydroxybut-1-en-1-yl)-5-oxocyclopentyl)ethyl)benzoic acid

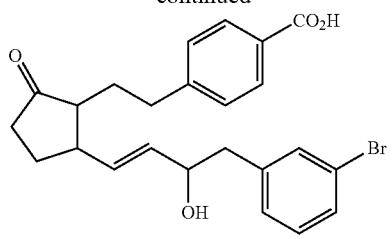

(E)-4-(2-(2-(4-(3-bromophenyl)-3-hydroxybut-1-en-1-yl)-5-oxocyclopentyl)ethyl)benzoic acid

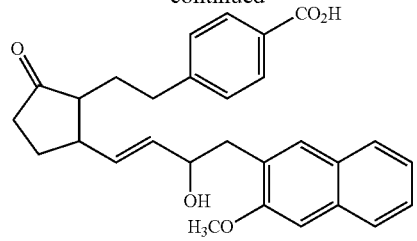

(E)-4-(2-(2-(3-hydroxy-4-(3-methoxynaphthalen-2-yl)but-1-en-1-yl)-5-oxocyclopentyl)ethyl)benzoic acid

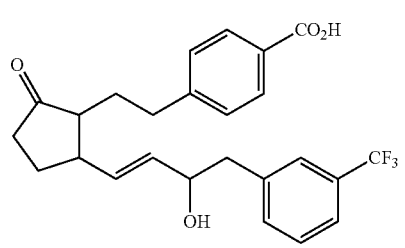

(E)-4-(2-(2-(3-hydroxy-4-(3-(trifluoromethyl)phenyl)but-1-en-1-yl)-5-oxocyclopentyl)ethyl)benzoic acid

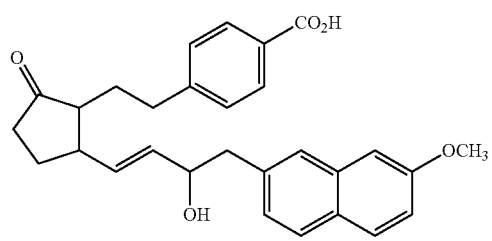

(E)-4-(2-(2-(3-hydroxy-4-(7-methoxynaphthalen-2-yl)but-1-en-1-yl)-5-oxocyclopentyl)ethyl)benzoic acid

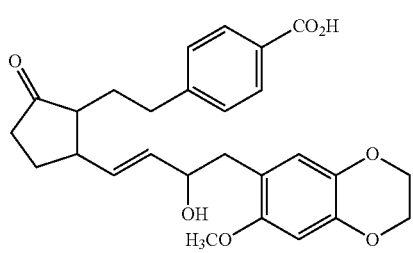

(E)-4-(2-(2-(3-hydroxy-4-(7-methoxy-2,3-dihydrobenzo[b][1,4]dioxin-6-yl)but-1-en-1-yl)-5-oxocyclopentyl)ethyl)benzoic acid

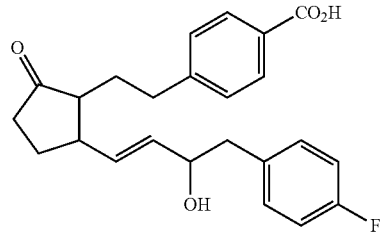

(E)-4-(2-(2-(4-(4-fluorophenyl)-3-hydroxybut-1-en-1-yl)-5-oxocyclopentyl)ethyl)benzoic acid

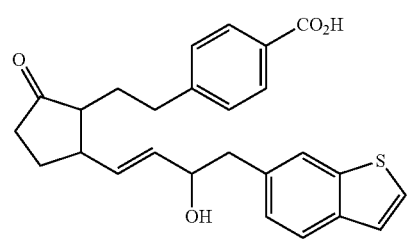

(E)-4-(2-(2-(4-benzo[b]thiophen-6-yl)-3-hydroxybut-1-en-1-yl)-5-oxocyclopentyl)ethyl)benzoic acid

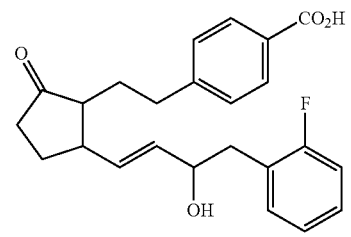

(E)-4-(2-(2-(4-(2-fluorophenyl)-3-hydroxybut-1-en-1-yl)-5-oxocyclopentyl)ethyl)benzoic acid

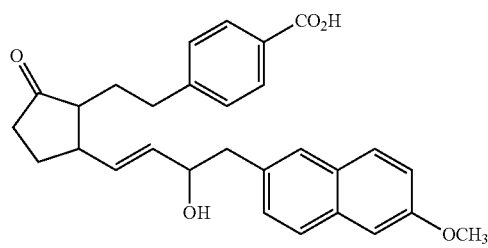

(E)-4-(2-(2-(3-hydroxy-4-(6-methoxynaphthalen-2-yl)but-1-en-1-yl)-5-oxocyclopentyl)ethyl)benzoic acid

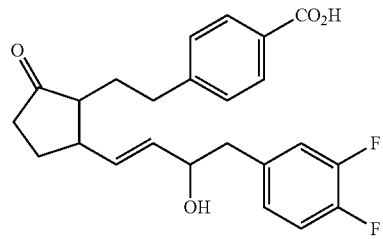

(E)-4-(2-(2-(4-(3,4-difluorophenyl)-3-hydroxybut-1-en-1-yl)-5-oxocyclopentyl)ethyl)benzoic acid

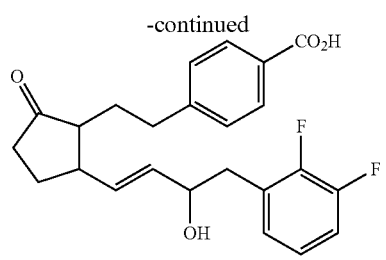

(E)-4-(2-(2-(4-(2,3-difluorophenyl)-3-hydroxybut-1-en-1-yl)-5-oxocyclopentyl)ethyl)benzoic acid

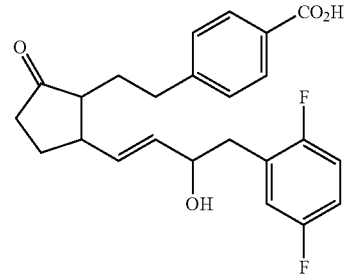

(E)-4-(2-(2-(4-(2,5-difluorophenyl)-3-hydroxybut-1-en-1-yl)-5-oxocyclopentyl)ethyl)benzoic acid In some embodiments, a compound described herein, such as an optionally substituted cyclopentanone, an optionally substituted 2,3-diarylalkyl cyclopentanone, a compound of Formula 1, 1a, 1b, 2, 3, 3a, 3b, or 4, optionally substituted (E)-4-(2-(2-(3-hydroxy-4-(naphthalen-2-yl)but-1-en-1-yl)-5-oxocyclopentyl)ethyl)benzoic acid; optionally substituted (E)-4-(2-(2-(4-(3-chlorobenzo[b]thiophen-2-yl)-3-hydroxybut-1-en-1-yl)-5-oxocyclopentyl)ethyl)benzoic acid; optionally substituted (E)-4-(2-(2-(4-(3-fluorophenyl)-3-hydroxybut-1-en-1-yl)-5-oxocyclopentyl)ethyl)benzoic acid; optionally substituted (E)-4-(2-(2-(4-(3-chlorophenyl)-3-hydroxybut-1-en-1-yl)-5-oxocyclopentyl)ethyl)benzoic acid; optionally substituted (E)-4-(2-(2-(4-(3-bromophenyl)-3-hydroxybut-1-en-1-yl)-5-oxocyclopentyl)ethyl)benzoic acid; optionally substituted (E)-4-(2-(2-(3-hydroxy-4-(3-(trifluoromethyl)phenyl)but-1-en-1-yl)-5-oxocyclopentyl)ethyl)benzoic acid; optionally substituted (E)-4-(2-(2-(3-hydroxy-4-(7-methoxy-2,3-dihydrobenzo[b][1,4]dioxin-6-yl)but-1-en-1-yl)-5-oxocyclopentyl)ethyl)benzoic acid; optionally substituted (E)-4-(2-(2-(4-(benzo[b]thiophen-6-yl)-3-hydroxybut-1-en-1-yl)-5-oxocyclopentyl)ethyl)benzoic acid; optionally substituted (E)-4-(2-(2-(3-hydroxy-4-(6-methoxynaphthalen-2-yl)but-1-en-1-yl)-5-oxocyclopentyl)ethyl)benzoic acid; optionally substituted (E)-4-(2-(2-(3-hydroxy-4-(3-methoxynaphthalen-2-yl)but-1-en-1-yl)-5-oxocyclopentyl)ethyl)benzoic acid; optionally substituted (E)-4-(2-(2-(3-hydroxy-4-(7-methoxynaphthalen-2-yl)but-1-en-1-yl)-5-oxocyclopentyl)ethyl)benzoic acid; optionally substituted (E)-4-(2-(2-(4-(4-fluorophenyl)-3-hydroxybut-1-en-1-yl)-5-oxocyclopentyl)ethyl)benzoic acid; optionally substituted (E)-4-(2-(2-(4-(2-fluorophenyl)-3-hydroxybut-1-en-1-yl)-5-oxocyclopentyl)ethyl)benzoic acid; optionally substituted (E)-4-(2-(2-(4-(3,4-difluorophenyl)-3-hydroxybut-1-en-1-yl)-5-oxocyclopentyl)ethyl)benzoic acid; optionally substituted (E)-4-(2-(2-(4-(2,3-difluorophenyl)-3-hydroxybut-1-en-1-yl)-5-oxocyclopentyl)ethyl)benzoic acid; or optionally substituted (E)-4-(2-(2-(4-(2,5-difluorophenyl)-3-hydroxybut-1-en-1-yl)-5-oxocyclopentyl)ethyl)benzoic acid, (referred to hereafter as a "subject compound") binds to a prostaglandin receptor, such as a prostaglandin EP4 receptor. The subject compound may be an agonist or an antagonist of the receptor.

In some embodiments, a subject compound binds to a prostaglandin EP4 receptor with a binding $EC_{50}$ value of about 10 µM or less, about 1 µM or less, about 200 nM or less, about 100 nM or less, about 50 nM or less, about 20 nM or less, about 10 nM or less, or about 1 nM or less, and may have $EC_{50}$ value as low as 10 µM, 1 µM, or 0.01 µM.

In some embodiments, a subject compound is a prostaglandin receptor agonist. For example, a subject compound may be an agonist of a prostaglandin EP4 receptor with a functional $EC_{50}$ value of about 10 µM or less, about 1 µM or less, about 200 nM or less, about 100 nM or less, about 50 nM or less, about 20 nM or less, about 10 nM or less, or about 1 nM or less, and may have an $EC_{50}$ value as low as 10 µM, 1 µM, or 0.01 pM.

In some embodiments, a subject compound is more active at the prostaglandin EP4 receptor than at any other prostaglandin receptor. For example, a subject compound may have a functional or binding $EC_{50}$ that is at least about 10 times, about 100 times, or at least about 1000 times lower, and may be up to 100,000 times lower, than the functional or binding $EC_{50}$ for the same compound at any other prostaglandin receptor.

Subject compounds can be used for reducing intraocular pressure. A subject compound can be administered systemically, topically to the eye, or by another route of administration, to a mammal in need thereof. Reduction of intraocular pressure can delay or prevent the onset of glaucoma, such as primary open angle glaucoma, and to delay or prevent further vision loss in patients with primary open angle glaucoma. Thus, subject compounds are also useful for treating glaucoma.

Subject compounds can also be used for growing hair. For example, a subject compound may be administered to a mammal in which hair growth is desired. Administration can be systemic, topical to the area in which hair growth is desired, or by another route of administration. Growing hair can include one or more of: increasing the number of individual hairs, increasing the length of individual hairs, and increasing the width or thickness of individual hairs. Subject compounds are also useful for improving the appearance of hair, including increasing its gloss, shine, or other properties related to the reflection or dispersion of light, as well as changing the color of hair, including changing hair from grey or white to the color the hair was before it turned grey or white, such as red, brown, or black.

For the purposes of this disclosure, "treat," "treating," or "treatment" includes use of a compound, composition, therapeutically active agent, or drug in the diagnosis, cure, mitigation, treatment, or prevention of disease or other undesirable condition.

A "pharmaceutically acceptable salt" includes any salt that retains the activity of the parent compound and is acceptable for pharmaceutical use. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring. (See, e.g., *Handbook of*

*Pharmaceutical Salts*, P. Heinrich Stahl & Camille G. Wermuth (Eds), Verlag; *Helvetica Chimica Acta*-Zürich, 2002, 329-345.) The term "pharmaceutically acceptable salt" is also meant to include salts of active compounds which are prepared with relatively nontoxic acids or bases, depending on the particular substituent moieties found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66:1-19). Certain specific compounds of the present invention may contain both basic and acidic functionalities that allow the compounds to be converted into either base or acid addition salts.

A prodrug includes a compound which is converted to a therapeutically active compound after administration, such as by hydrolysis of an ester group or some other biologically labile group. Ester prodrugs of the subject compounds are specifically contemplated. An ester may be derived from a carboxylic acid of C1 (i.e. the terminal carboxylic acid of a natural prostaglandin), or an ester may be derived from a carboxylic acid functional group on another part of the molecule, such as on a phenyl ring. Some examples of useful esters can include an alkyl ester, a hydroxyalkyl ester, a morpholinoalkyl ester, an aryl ester, or a heteroaryl ester. Prodrug preparation is well known in the art. For example, "Prodrugs and Drug Delivery Systems," which is a chapter in Richard B. Silverman, *Organic Chemistry of Drug Design and Drug Action*, 2d Ed., Elsevier Academic Press: Amsterdam, 2004, pp. 496-557, provides further detail on the subject.

Those skilled in the art will readily understand that for administration or the manufacture of medicaments, subject compounds can be admixed with pharmaceutically acceptable excipients. Specifically, a drug to be administered systemically, it may be confected as a powder, pill, tablet or the like, or as a solution, emulsion, suspension, aerosol, syrup or elixir suitable for oral or parenteral administration or inhalation.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Liquid pharmaceutically administrable dosage forms can, for example, comprise a solution or suspension of one or more of the subject compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the subject compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the subject compound or compounds administered is dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the subject compounds may be in the range of about 0.5 or about 1 to about 100 mg/kg/day.

A liquid which is ophthalmically acceptable includes a liquid that is formulated such that it can be administered topically to the eye. The comfort can be a consideration, although sometimes formulation considerations (e.g. drug stability) may necessitate less than optimal comfort. In the case that comfort is not ideal, the liquid can be formulated such that the liquid is tolerable to the patient for topical ophthalmic use. Additionally, an ophthalmically acceptable liquid can be packaged for single use, or contain a preservative to prevent contamination over multiple uses.

For ophthalmic application, solutions or medicaments are often prepared using a physiological saline solution as a major vehicle. Ophthalmic solutions can be maintained at a comfortable pH with an appropriate buffer system. The formulations may also contain conventional, pharmaceutically acceptable preservatives, stabilizers and surfactants.

Preservatives that may be used in pharmaceutical compositions include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used in an ophthalmically acceptable liquid. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the an ophtalmically acceptable liquids include, but are not limited to, sodium metabisulfite, sodium thiosulfate, acetylcysteine, butylated hydroxyanisole and butylated hydroxytoluene.

Other excipient components which may be included in ophthalmic preparations are chelating agents. A useful chelating agent is edetate disodium, although other chelating agents may also be used in place or in conjunction with it.

Some ophthalmically acceptable liquid dosage forms include ingredients having the following amounts:

| Ingredient | Amount (% w/v) |
| --- | --- |
| subject compound | about 0.001-5 |
| preservative | 0-0.10 |
| vehicle | 0-40 |
| tonicity adjuster | 1-10 |
| buffer | 0.01-10 |
| pH adjuster | q.s. pH 4.5-7.5 |
| antioxidant | as needed |
| surfactant | as needed |
| purified water | as needed to make 100% |

For topical use, creams, ointments, gels, solutions or suspensions, etc., containing subject compounds are employed. Topical formulations can include a pharmaceutical carrier, co-solvent, emulsifier, penetration enhancer, preservative system, or emollient.

The actual dose of a subject compound depends on factors such as the specific compound, and on the condition to be treated. The selection of the appropriate dose is well within the skill of the skilled artisan with the benefit of this disclosure.

For treatment of diseases affecting the eye including glaucoma, subject compounds can be administered topically, periocularly, intraocularly, or by any other effective means known in the art.

In one embodiment, the subject compounds can be useful in the treatment of baldness and/or hair loss. Alopecia (baldness) is a deficiency of either normal or abnormal hair, and is primarily a cosmetic problem in humans. It is a deficiency of terminal hair, the broad diameter, colored hair that is readily seen. However, in the so called bald person, although there is a noticeable absence of terminal hair, the skin does contain vellus hair, which is a fine colorless hair which may require microscopic examination to determine its presence. This vellus hair is a precursor to terminal hair.

The subject compounds can be used to stimulate, such as the conversion of vellus hair to growth as terminal hair, as well as increasing the rate of growth of terminal hair.

The subject compounds can also be used to stimulate growth of eye lashes. Application of a subject compound to an eye or an eyelid can result in lashes that are longer and have a fuller, denser appearance in the treated eye. The changes in the lashes may be apparent on gross inspection. Possible changes to lashes can include increased length of lashes, increased number of lashes along the normal lash line, increased thickness and luster of lashes, increased auxiliary lash-like terminal hair in transitional areas adjacent to areas of normal lash growth, increased auxiliary lash-like terminal hairs at the medial and lateral canthal area, increased pigmentation of the lashes, increased numbers, increased length, as well as increased luster, and thickness of fine hair on the skin of the adjacent lid, and finally, increased perpendicular angulation from the skin surface.

In one embodiment, the subject compound is mixed with a dermatologically compatible vehicle or carrier. The vehicle, which may be employed for preparing compositions as described herein, may comprise, for example, aqueous solutions such as e.g., physiological salines, oil solutions, or ointments. The vehicle furthermore may contain dermatologically compatible preservatives such as e.g., benzalkonium chloride, surfactants like e.g., polysorbate 80, liposomes or polymers, for example, methyl cellulose, polyvinyl alcohol, polyvinyl pyrrolidone and hyaluronic acid; these may be used for increasing the viscosity. Furthermore, it is also possible to use soluble or insoluble drug inserts when the drug is to be administered.

In one embodiment, dermatological compositions can be formulated for topical treatment for the stimulation of hair growth which comprises an effective hair growth simulating amount of one or more subject compounds and a dermatologically compatible carrier. Effective amounts of the subject compounds may be determined by one of ordinary skill in the art, but will vary depending on the compound employed, frequency of application and desired result. The subject compound will generally range from about 0.0000001 to about 50% by weight; about 0.001 to about 50% by weight; or about 0.1 to about 30% by weight of the dermatological composition.

In one embodiment, the application of the subject compounds for stimulation of hair growth finds applications in mammalian species, including both humans and animals. In humans, the subject compounds can be applied for example, to the scalp, face beard, head, pubic area, upper lip, eyebrows, and eyelids. In animal raised for their pelts, e.g., mink, the subject compounds can be applied over the entire surface of the body to improve the overall pelt for commercial reasons. The process can also be used for cosmetic reasons in animals, e.g., applied to the skin of dogs and cats having bald patches due to mange or other diseases causing a degree of alopecia.

The pharmaceutical compositions contemplated for the stimulation of hair growth include pharmaceutical compositions suited for topical and local action. The term "topical" as employed with respect to hair growth relates to the use of a subject compound incorporated in a suitable pharmaceutical carrier, and applied at the site of thinning hair or baldness for exertion of local action. Accordingly, such topical compositions include those pharmaceutical forms in which the subject compound is applied externally by direct contact with the skin to be treated. Conventional pharmaceutical forms for this purpose include ointments, liniments, creams, shampoos, lotions, pastes, jellies, sprays, aerosols, and the like, and may be applied in patches or impregnated dressings depending on the part of the body to be treated. The term "ointment" embraces formulations (including creams) having oleaginous, water-soluble and emulsion-type bases, e.g., petrolatum, lanolin, polyethylene glycols, as well as mixtures of these.

Typically, the subject compounds can be applied repeatedly for the sustained period of time topically on the part of the body to be treated, for example, the eyelids, eyebrows, skin or scalp. The preferred dosage regimen will generally involve regular, such as daily, administration for a period of treatment of at least one month, at least three months, or at least six months.

For topical use on the eyelids or eyebrows, the subject compounds can be formulated in aqueous solutions, creams, ointments, or oils exhibiting physiologically acceptable osmolarity by addition of pharmaceutically acceptable buffers and salts. such formulations may or may not, depending on the dispenser, contain preservatives such as benzalkonium chloride, chlorhexidine, chlorobutanol, parahydroxybenzoic acids and phenylmercuric salts such as nitrate, chloride, acetate, and borate, or antioxidants, as well as additives like EDTA, sorbitol, boric acid and the like as additives. Furthermore, particularly aqueous solutions may contain viscosity increasing agents such as polysaccharides, e.g., methylcellulose, mucopolysaccharides, e.g., hyaluronic acid and chondroitin sulfate, or poly alcohol, e.g., polyvinylalcohol. Various slow releasing gels and matricies may also be employed as well as soluble and insoluble ocular inserts, for instance, based on substances forming in situ gels. Depending on the actual formation and compound to be used, various amounts of the drug and different dose regimens may be employed. Typically, the daily amount of subject compound for treatment of the eyelid may be about 0.1 ng to about 100 mg per eyelid.

For topical use on the skin and scalp, the subject compound can be advantageously formulated using ointments, creams, liniments or patches as a carrier of the active ingredient. Also, these formulations may or may not contain preservatives, depending on the dispenser and nature of use. Such preservatives include those mentioned above, and methyl-, propyl-, or butyl-parahydroxybenzoic acid, betaine, chlorhexidine, benzalkonium chloride, and the like. Various matrices for the slow release delivery may also be used. Typically, the dose to be applied on the scalp is in the range of about 0.1 ng to about 100 mg per day, more preferably about 1 ng to about 10 mg per day, and most preferably about 10 ng to about 1 mg per day depending on the subject compound and the formulation. To achieve the daily amount of medication depending on the formulation, the subject compound may be administered once or several times daily with or without antioxidants.

EXAMPLES

Scheme 1-Synthesis of Substituted Ethyl Alcohols:

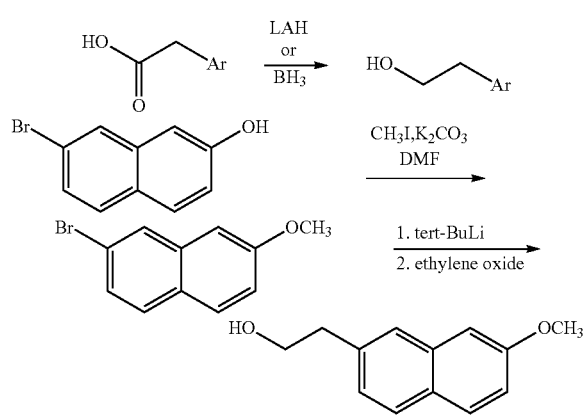

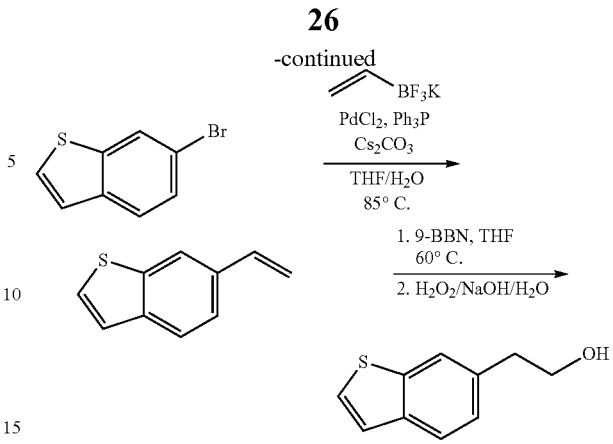

Synthetic Methods

Substituted Ethyl Alcohol Synthesis-Representative Procedures (Scheme 1)
2-(3-Chlorobenzo[b]thiophen-2-yl)ethanol General Procedure for LiAlH$_4$ Reduction of Carboxilic Acids

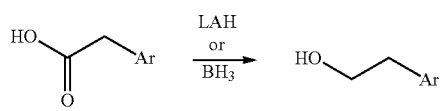

Lithium aluminum hydride (3.4 mL, 6.8 mmol, 2 M/THF) was added to a 0° C. solution of 2-(3-chlorobenzo[b]thiophen-2-yl)acetic acid (1.006 g, 4.44 mmol) in 50 mL THF. The reaction was allowed to warm to room temperature and after 2 h, was recooled to 0° C. and quenched by addition of 10 mL H$_2$O. NaOH solution (20 mL, 3 M) was added and the mixture was allowed to warm to room temperature. After 30 minutes, brine was added and the resulting mixture was extracted with ethyl acetate (3×100 mL). The combined ethyl acetate solution was dried (Na$_2$SO$_4$), filtered and evaporated. Purification by flash chromatography gave the title compound (1.053 g, 92%).

The other analogous alcohols were synthesized using the procedure above, with the following exceptions (Scheme 1):

2-(2,3-dihydrobenzo[b][1,4]dioxin-6-yl)ethanol

BH$_3$.THF (44 mL, 44 mmol, 1 M/THF) was added to a 0° C. solution of 2-(2,3-dihydrobenzo[b][1,4]dioxin-6-yl)acetic acid (3.419 g, 17.6 mmol) in THF (8.8 mL). The reaction was allowed to warm to room temperature and after 2 h, 20 mL H$_2$O was added slowly by syringe. The resulting mixture was extracted with ethyl acetate, the organic portion was washed with brine, and then was dried (Na$_2$SO$_4$), filtered and evaporated. Purification by flash chromatography (ethyl acetate/hexanes) gave the title compound (3.059 g, 99%).

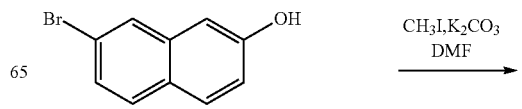

2-Bromo-7-methoxynaphthalene

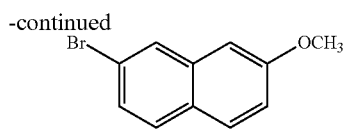

Methyl iodide (2 mL, 32.1 mmol) was added to a mixture of 7-bromonaphthalen-2-ol (6.26 g, 28.0 mmol) and $K_2CO_3$ (4.62 g, 33.4 mmol) in DMF (21 mL). After stirring for 3 days, the mixture was partitioned between ethyl acetate/H2O and the organic solution was further washed with $H_2O$ (5×60 mL). The organic solution was then dried ($Na_2SO_4$), filtered and evaporated. Purification by flash chromatography (ethyl acetate/hexanes) gave the title compound (6.41 g, 96%).

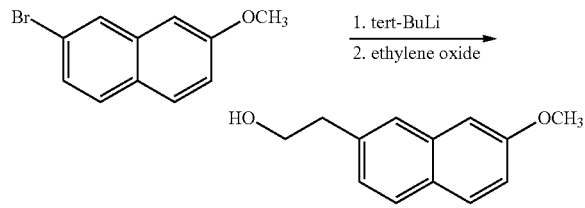

2-(6-methoxynaphthalen-2-yl)ethanol tert-Butyllithium (5.2 mL, 8.84 mmol, 1.7 M/pentane) was added to a −78° C. solution of 2-bromo-6-methoxynaphthalene (1.0471 g, 4.42 mmol) in THF (10 mL)/ether (10 mL). After 30 minutes, a solution of ethylene oxide in THF (2 mL, 23 mmol, 0.5 g/mL) was added and the reaction was allowed to warm to room temperature. After overnight stirring, 30 mL saturated $NH_4Cl$ solution was added and the resulting mixture was extracted with ethyl acetate (3×30 mL). The combined organic solution was then dried ($Na_2SO_4$), filtered and evaporated. Purification by flash chromatography (ethyl acetate/hexanes) gave the title compound (478 mg, 53%).

2-(7-methoxynaphthalen-2-yl)ethanol

The title compound was synthesized as described above from 2-bromo-7-methoxynaphthalene and ethylene oxide.

2-(3-methoxynaphthalen-2-yl)ethanol

The title compound was synthesized as described above from 2-bromo-3-methoxynaphthalene and ethylene oxide.

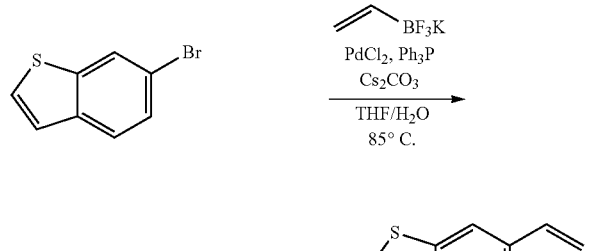

6-vinylbenzo[b]thiophene

A mixture of 6-bromobenzo[b]thiophene (217 mg, 1.02 mmol), potassium vinyltrifluoroborate (137 mg, 1.02 mmol), $Cs_2CO_3$ (983 mg, 3.02 mmol), $Ph_3P$ (17 mg, 0.066 mmol) and $PdCl_2$ (5 mg, 0.028 mol) in THF (1.8 mL)/$H_2O$ (0.2 mL) was heated at 85° C. After overnight stirring, $H_2O$ (5 mL) and saturated $NH_4Cl$ solution (50 mL) were added and the resulting mixture was extracted with $CH_2Cl_2$ (3×25 mL). The combined organic solution was dried ($Na_2SO_4$), filtered and evaporated. Purification by flash chromatography (ethyl acetate/hexanes) gave the title compound (67 mg, 41%).

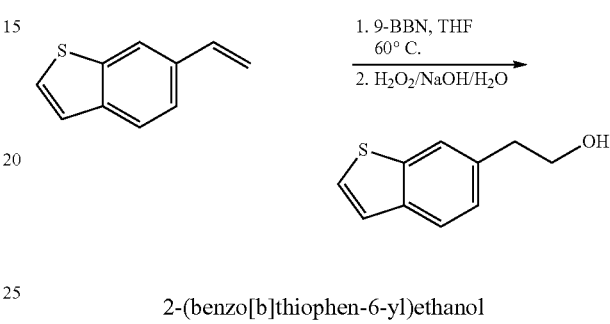

2-(benzo[b]thiophen-6-yl)ethanol

A solution of 6-vinylbenzo[b]thiophene (2.124 g, 13.3 mmol) in 80 mL THF was added to a solution of 9-borabicyclo[3.3.1]nonane (9-BBN) (5.21 g, 21.3 mmol) in 80 mL THF, rinsing with 5 mL THF. The solution was heated at 60° C. for 2.5 h and then a solution of $H_2O_2$ (36 mL, 35%)/NaOH (36 mL. 0.5 M)/$H_2O$ (9 mL) was added slowly. The reaction was then heated to 85° C. for 1 h, cooled to room temperature and 50 mL $H_2O$ was added. The mixture was extracted with ethyl acetate (3×50 mL), the combined organic solution was washed with brine and then was dried ($Na_2SO_4$), filtered and evaporated. Purification by flash chromatography (ethyl acetate/hexanes) gave the title compound (2.338 g, 99%).

Scheme 2-Synthesis of Lower Chain

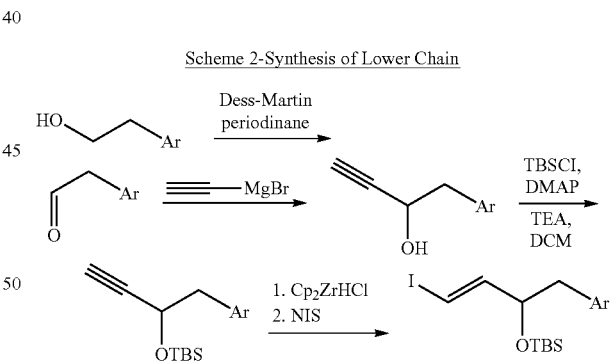

Lower Chain Synthesis-Representative Procedures
(Scheme 2)

2-(3-chlorobenzo[b]thiophen-2-yl)acetaldehyde

Dess-Martin period inane (1.570 g, 3.70 mmol) was added to an ice-cold solution of 2-(benzo[b]thiophen-6-yl)ethanol (649 mg, 3.05 mmol) in $CH_2Cl_2$ (8 mL). The reaction was allowed to warm to room temperature and after 2 h, was poured into a mixture of 50 mL saturated $NaHCO_3$/50 mL 5% $NaHSO_3$ solution. The resulting mixture was stirred for 30 minutes and then was extracted with $CH_2Cl_2$ (3×40 mL). The combined organic solution was dried (Na$_2$SO$_4$), filtered and evaporated to give the title compound which was used directly in the next step.

1-(3-chlorobenzo[b]thiophen-2-yl)but-3-yn-2-ol

A solution of 2-(3-chlorobenzo[b]thiophen-2-yl)acetaldehyde (1.100 g, 5.60 mmol) in 10 mL THF was added dropwise (cannula) to an ice-cold solution of the ethynylmagnesium bromide (25 mL, 12.5 mmol, 0.5 M/THF). The reaction was stirred for 1 h at 0° C. and for 1 h at room temperature and then was quenched by addition of 100 mL saturated NH$_4$Cl solution. The resulting mixture was extracted with ethyl acetate (3×) and the combined organic solution was dried (Na$_2$SO$_4$), filtered and evaporated. Purification by flash chromatography (ethyl acetate/hexanes) gave the title compound (475 mg, 65%).

tert-butyl((1-(3-chlorobenzo[b]thiophen-2-yl)but-3-yn-2-yl)oxy)dimethylsilane

DMAP (130 mg) TBSCl (603 mg) and triethylamine (350 mL) were added to a solution of 1-(3-chlorobenzo[b]thiophen-2-yl)but-3-yn-2-ol (475 mg, 1.99 mmol) in CH$_2$Cl$_2$ (6.4 mL). The reaction was stirred overnight and then 20 mL saturated NH$_4$Cl solution was added. The resulting mixture was extracted with CH$_2$Cl$_2$ (3×20 mL) and the combined organic solution was dried (Na$_2$SO$_4$), filtered and evaporated. Purification by flash chromatography (ethyl acetate/hexanes) gave the title compound (565 mg, 81%).

(E)-tert-butyl((1-(3-chlorobenzo[b]thiophen-2-yl)-4-iodobut-3-en-2-yl)oxy)dimethylsilane Cp$_2$ZrHCl (628 mg, 2.5 mmol) was added to a solution of tert-butyl((1-(3-chlorobenzo[b]thiophen-2-yl)but-3-yn-2-yl)oxy)dimethylsilane (565 mg, 1.61 mmol) in CH$_2$Cl$_2$ (11 mL). The reaction was stirred for 1 h and then N-iodosuccinimide (585 mg, 2.6 mmol) was added. After 30 minutes, 30 mL saturated NaHCO$_3$ solution was added and the resulting mixture was extracted with CH$_2$Cl$_2$ (3×30 mL). The combined organic solution was dried (Na$_2$SO$_4$), filtered and evaporated. Purification by flash chromatography (ethyl acetate/hexanes) gave the title compound (669 mg, 87%).

Scheme 3-Representative Procedures

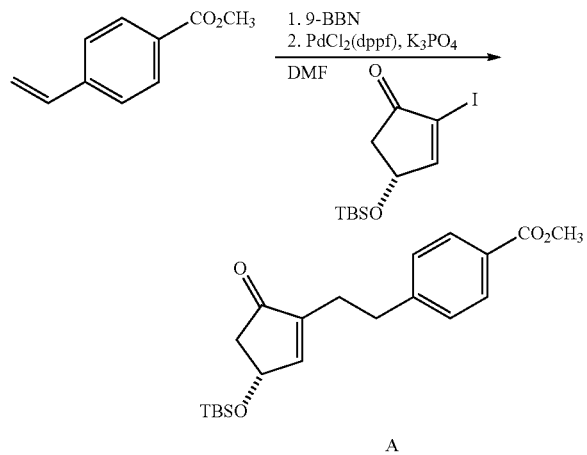

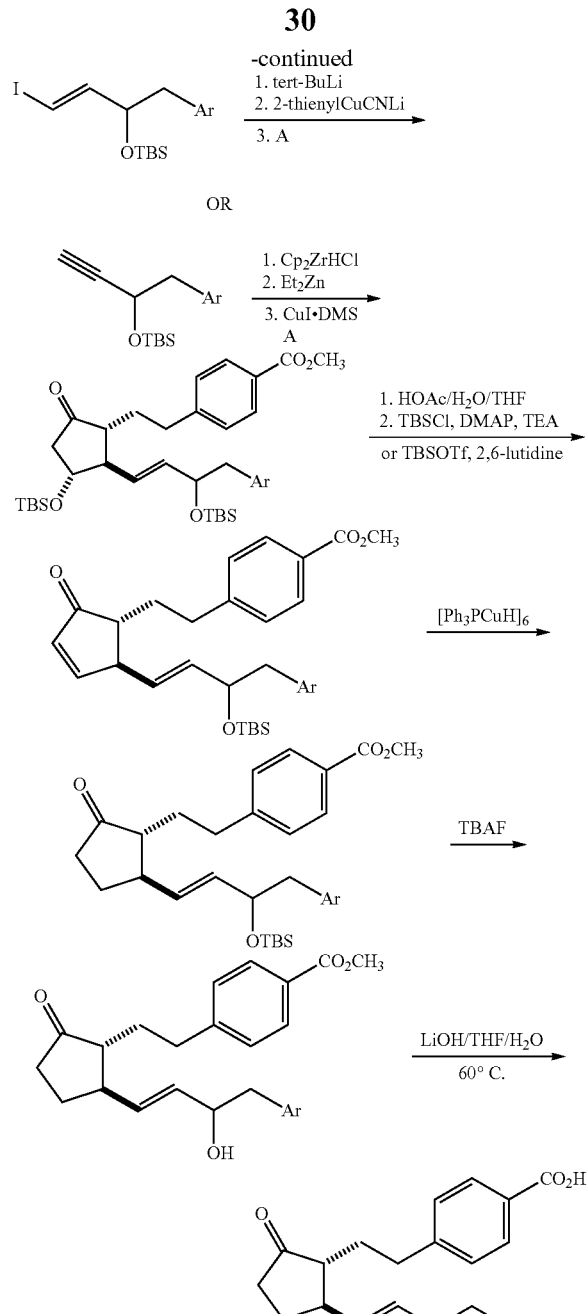

(R)-4-((tert-butyldimethylsilyl)oxy)-2-iodocyclopent-2-enone

The procedure described in Johnson, C. R., Braun, M. P. *J. Am. Chem Soc.* 1993, 115, 11014 was followed with modification. A solution of I$_2$ (6.55 g, 25.8 mmol) and pyridine (12 mL) in CH$_2$Cl$_2$ (12 mL) was cannula transferred to a 0° C. solution of (R)-4-((tert-butyldimethylsilyl)oxy)cyclopent-2-enone (3.17 g, 14.9 mmol) and pyridine (5.4 mL) in CH$_2$Cl$_2$ (5.4 mL). The reaction was allowed to warm to room temperature and after 2 h, 100 mL 1 M HCl was added. The resulting mixture was extracted with CH$_2$Cl$_2$ (3×60 mL) and the combined organic solution was washed with 100 mL saturated NaHSO$_3$ solution and 50 mL brine and then was dried (Na$_2$SO$_4$), filtered and evaporated. Purification by flash chromatography (ethyl acetate/hexanes) gave the title compound (4.997 g, 99%).

(R)-methyl 4-(2-(3-((tert-butyldimethylsilyl)oxy)-5-oxocyclopent-1-en-1-yl)ethyl)benzoate (A)

A solution of 9-BBN (6.95 g, 28.5 mmol) in 110 mL THF was cannula transferred to a solution of methyl 4-vinylbenzoate (4.65 g, 28.7 mmol) in 22 mL THF, rinsing with 10 mL THF. The reaction was stirred at room temperature for 4 h, was cooled to 0° C. and 5.4 mL H$_2$O was added. After 45 minutes at room temperature, the solution was cannula transferred to a mixture of the (R)-4-(((tert-butyldimethylsilyl)oxy)-2-iodocyclopent-2-enone (8 g, 24 mmol) and PdCl$_2$(dppf).CH$_2$Cl$_2$ (1.76 g, 2.41 mmol) in DMF (70 mL). The reaction was stirred for 5 minutes and then a solution of K$_3$PO$_4$ (9.6 mL, 28.8 mmol, 3 M) was added. The resulting dark mixture was allowed to stir overnight and then was partitioned between ethyl acetate/H$_2$O. The organic solution was washed further with H$_2$O (2×) and brine and then was dried (Na$_2$SO$_4$), filtered and evaporated. Purification by flash chromatography (ethyl acetate/hexanes) gave the title compound (6.81 g).

Methyl 4-(2-((1R,2R,3R)-3-((tert-butyldimethylsilyl)oxy)-2-((E)-3-((tert-butyldimethylsilyl)oxy)-4-(naphthalen-2-yl)but-1-en-1-yl)-5-oxocyclopentyl)ethyl)benzoate (Table 1 entries 1-14)

n-Butyllithium (2.0 mL, 3.2 mmol, 1.6 M/hexanes) was added to a solution of thiophene (280 mL, 3.54 mmol) in THF (3.3 mL) at −78° C. The reaction was stirred for 1 h at 0° C. and then was cannula transferred to a −78° C. mixture of CuCN (318 mg, 3.55 mmol) in THF (3.2 mL). The resulting mixture was stirred for 1 h at room temperature.

In another flask, tert-butyllithium (4 mL, 6.8 mmol, 1.7 M/pentane) was added to a −78° C. solution of the vinyl iodide (1.527 g, 3.48 mmol) in ether (8.8 mL). After 30 minutes, the above 2-thienylCuCNLi solution was added by cannula and the reaction was allowed to warm to 0° C. After 15 minutes, the reaction was cooled to −78° C. and a solution of (R)-methyl 4-(2-(3-((tert-butyldimethylsilyl)oxy)-5-oxocyclopent-1-en-1-yl)ethyl)benzoate (1.054 g, 2.81 mmol) in ether (4 mL) was added dropwise by cannula, rinsing with 2 mL ether. The reaction was stirred at −78° C. for 5 minutes, was stirred at room temperature for 1 h and then was quenched by addition of 40 mL saturated NH$_4$Cl solution. The resulting mixture was extracted with ethyl acetate (3×40 mL) and the combined organic solution was dried (Na$_2$SO$_4$), filtered and evaporated. Purification by flash chromatography (ethyl acetate/hexanes) gave the title compound (1 g, 52%).

Methyl 4-(2-((1R,2R,3R)-2-((E)-4-(benzo[b]thiophen-6-yl)-3-((tert-butyldimethylsilyl)oxy)but-1-en-1-yl)-3-((tert-butyldimethylsilyl)oxy)-5-oxocyclopentyl)ethyl)benzoate (Table 1 entries 15-28)

The procedure from Bergdahl, M.; El-Batta, A. *Tetrahedron. Lett.* 2007, 48, 1761 was followed. A solution of ((1-(benzo[b]thiophen-6-yl)but-3-yn-2-yl)oxy)(tert-butyl)dimethylsilane (680 mg, 2.15 mmol) in CH$_2$Cl$_2$ (12 mL) was added to Cp$_2$ZrHCl (569 mg, 2.21 mmol) by cannula. The reaction was stirred for 30 minutes and then was cooled to −78° C. Diethylzinc (2 mL, 2.10 mmol, 15%/toluene) was added, the reaction was stirred at 0° C. for 15 minutes, and then (CuI)$_4$.3(Me$_2$S) (208 mg, 0.22 mmol) was added. The reaction was stirred further for 15 minutes and then a solution of the enone (766 mg, 2.05 mmol) in CH$_2$Cl$_2$ (2 mL) was added dropwise by cannula, rinsing with 1 mL CH$_2$Cl$_2$. The reaction was stirred for 5 minutes at 0° C., 5 minutes at room temperature and then overnight at 35° C. The reaction was then cooled to 0° C. and 5 mL H$_2$O was added. Ethyl acetate was added and the resulting mixture was filtered through a pad of Celite. The filtrate was washed with saturated NaHCO$_3$ solution (50 mL) and brine (50 mL) and then was dried (Na$_2$SO$_4$), filtered and evaporated. Purification by flash chromatography (ethyl acetate/hexanes) gave the title compound (417 mg, 29%).

Methyl 4-(2-((1R,2S)-2-((E)-3-((tert-butyldimethylsilyl)oxy)-4-(naphthalen-2-yl)but-1-en-1-yl)-5-oxocyclopent-3-en-1-yl)ethyl)benzoate (Scheme 3)

A mixture of methyl 4-(2-((1R,2R,3R)-3-((tert-butyldimethylsilyl)oxy)-2-((E)-3-((tert-butyldimethylsilyl)oxy)-4-(naphthalen-2-yl)but-1-en-1-yl)-5-oxocyclopentyl)ethyl)benzoate (1 g, 1.46 mmol) in HOAc/H$_2$O/THF (32 mL, 2:1:1) was stirred at 70° C. overnight and then was co-evaporated with toluene. Purification of the residue by flash chromatography (ethyl acetate/hexanes) gave methyl 4-(2-((1R,2S)-2-((E)-3-hydroxy-4-(naphthalen-2-yl)but-1-en-1-yl)-5-oxocyclopent-3-en-1-yl)ethyl)benzoate (497 mg, 77%).

Reprotection of the C-15 alcohol was accomplished as described above for tert-butyl((1-(3-chlorobenzo[b]thiophen-2-yl)but-3-yn-2-yl)oxy)dimethylsilane to give the title compound (464 mg, 57%).

Methyl 4-(2-((1R,2R)-2-((E)-3-((tert-butyldimethylsilyl)oxy)-4-(naphthalen-2-yl)but-1-en-1-yl)-5-oxocyclopentyl)ethyl)benzoate (Scheme 3)

A solution of methyl 4-(2-((1R,2S)-2-((E)-3-((tert-butyldimethylsilyl)oxy)-4-(naphthalen-2-yl)but-1-en-1-yl)-5-oxocyclopent-3-en-1-yl)ethyl)benzoate (111 mg, 0.20 mmol) in toluene (1.6 mL) was added dropwise by cannula to a −40° C. mixture of [Ph$_3$PCuH]$_6$ (205 mg, 0.11 mmol) in toluene (9.8 mL), rinsing with 0.4 mL toluene. The reaction was stirred at −40° C. for 1 h and then at room temperature overnight. Saturated NH$_4$Cl solution (20 mL) was added and the resulting mixture was extracted with ethyl acetate (3×20 mL). The combined organic solution was dried (Na$_2$SO$_4$), filtered and evaporated. Purification by flash chromatography (ethyl acetate/hexanes) gave the title compound (91 mg, 82%).

Methyl 4-(2-((1R,2R)-2-((E)-3-hydroxy-4-(naphthalen-2-yl)but-1-en-1-yl)-5-oxocyclopentyl)ethyl)benzoate (Scheme 3)

TBAF (500 mL, 0.5 mmol, 1 M/THF) was added to a solution of the TBS ether (91 mg, 0.16 mmol) in THF (1.3 mL). After overnight stirring, saturated NH$_4$Cl solution (20 mL) was added and the resulting mixture was extracted with ethyl acetate (3×). The combined organic solution was dried (Na$_2$SO$_4$), filtered and evaporated. Purification by flash chromatography (ethyl acetate/hexanes) gave the title compound (60 mg, 86%).

4-(2-((1R,2R)-2-((E)-3-hydroxy-4-(naphthalen-2-yl)but-1-en-1-yl)-5-oxocyclopentyl)ethyl)benzoic acid (Scheme 3)

LiOH (240 mL, 0.24 mmol, 1 M) was added to a solution of methyl 4-(2-((1R,2R)-2-((E)-3-hydroxy-4-(naphthalen-2-yl)but-1-en-1-yl)-5-oxocyclopentyl)ethyl)benzoate (21 mg, 0.047 mmol) in THF (2.5 mL). The mixture was stirred at 60° C. overnight, cooled to room temperature and then 1 M HCl (20 mL) was added. The resulting mixture was extracted with CH₂Cl₂ (3×20 mL) and the combined organic solution was washed with brine and then was dried (Na₂SO₄), filtered and evaporated. Purification by preparative thin layer chromatography (10% methanol/CH₂Cl₂) gave the title compound (13 mg).

A person of ordinary skill in the art can prepare the subject compounds by using the methods disclosed herein, by adaptations readily ascertainable by those in the art from the disclosure herein, and/or by the knowledge generally available in the art as applied to the present disclosure.

In Vitro Testing

U.S. patent application publication No. 20070129552, published on Jun. 7, 2007, incorporated by reference herein, describes the methods used to obtain the in vitro data in Table 1 below.

| Entry | STRUCTURE | EP2 cAMP $EC_{50}$ (nM) | EP2 Ki (nM) | EP4 cAMP $EC_{50}$ (nM) | EP4 Ki $EC_{50}$ (nM) | OTHER RECEPTORS FLIPR $EC_{50}$ (nM) |
|---|---|---|---|---|---|---|
| 1 | 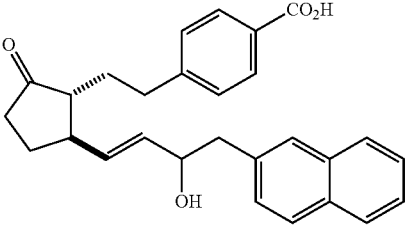 [SMILES: O=C(O)c1ccc(CC[C@H]2C(=O)CC[C@@H]2/C=C/C(O)Cc2ccc3ccccc3c2)cc1] faster eluting diastereomer | >10K | | 1 | 0.8 | NA: DP, EP1, EP3, FP, IP, TP |
| 2 | 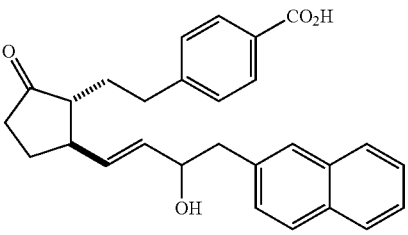 [SMILES: O=C(O)c1ccc(CC[C@H]2C(=O)CC[C@@H]2/C=C/C(O)Cc2ccc3ccccc3c2)cc1] slower eluting diastereomer | >10K | | 21 | 10 | NA: DP, EP1, EP3, FP, IP, TP |
| 3 | 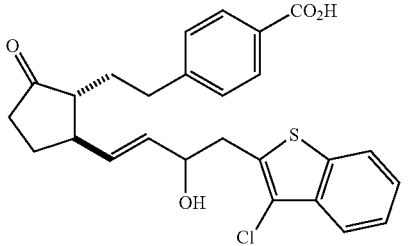 [SMILES: O=C(O)c1ccc(CC[C@H]2C(=O)CC[C@@H]2/C=C/C(O)Cc2sc3ccccc3c2Cl)cc1] faster eluting diastereomer | >10K | >10K | 1281 | 2314 | |
| 4 | 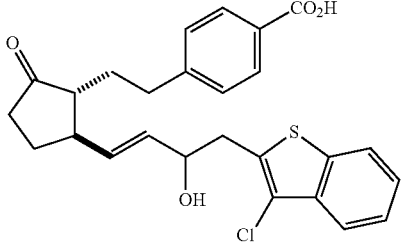 [SMILES: O=C(O)c1ccc(CC[C@H]2C(=O)CC[C@@H]2/C=C/C(O)Cc2sc3ccccc3c2Cl)cc1] slower eluting diastereomer | >10K | >10K | 186 | 603 | |

| Entry | STRUCTURE | EP2 cAMP EC$_{50}$ (nM) | EP2 Ki (nM) | EP4 cAMP EC$_{50}$ (nM) | EP4 Ki EC$_{50}$ (nM) | OTHER RECEPTORS FLIPR EC$_{50}$ (nM) |
|---|---|---|---|---|---|---|
| 5 | *faster eluting diastereomer* (3-F aryl) | 78 | 3420 | 1 | 40 | NA: DP, EP1, EP3, FP, IP, TP |
| 6 | *slower eluting diastereomer* (3-F aryl) | 10 | 1776 | 0.04 | 2 | EP3 (721), TP (7191) NA: DP, EP1, FP, IP |
| 7 | *faster eluting diastereomer* (3-Cl aryl) | 123 | 2755 | 2 | 2 | TP (4832) NA: DP, EP1, EP3, FP, IP |
| 8 | *slower eluting diastereomer* (3-Br aryl) | 8 | 1175 | 0.05 | 1 | EP3 (177), TP (100) NA: DP, EP1, FP, IP |
| 9 | *faster eluting diastereomer* (3-Br aryl) | 278 | 1446 | 12 | 105 | NA: DP, EP1, EP3, FP, IP, TP |

-continued

| Entry | STRUCTURE | EP2 cAMP EC$_{50}$ (nM) | EP2 Ki (nM) | EP4 cAMP EC$_{50}$ (nM) | EP4 Ki EC$_{50}$ (nM) | OTHER RECEPTORS FLIPR EC$_{50}$ (nM) |
|---|---|---|---|---|---|---|
| 10 | *3-Br phenyl compound, slower eluting diastereomer* | 26 | 947 | 0.2 | 1 | EP3 (180), TP (108) NA: DP, EP1, EP3, FP, IP |
| 11 | *3-CF$_3$ phenyl compound, faster eluting diastereomer* | 1014 | 3159 | 16 | 90 | NA: DP, EP1, EP3, FP, IP, TP |
| 12 | *3-CF$_3$ phenyl compound, slower eluting diastereomer* | 35 | 1310 | 0.2 | 1 | TP (218) NA: DP, EP1, EP3, FP, IP |
| 13 | *benzodioxane compound, faster eluting diastereomer* | >10K | 142 | 1019 | | |
| 14 | *benzodioxane compound, slower eluting diastereomer* | >10K | 8 | 81 | | |

-continued

| Entry | STRUCTURE | EP2 cAMP EC$_{50}$ (nM) | Ki (nM) | EP4 cAMP EC$_{50}$ (nM) | Ki EC$_{50}$ (nM) | OTHER RECEPTORS FLIPR EC$_{50}$ (nM) |
|---|---|---|---|---|---|---|
| 15 | | >10K | | 0.5 | 41 | EP3 (67), TP (<10K) NA: DP, EP1, FP, IP |
| 16 | | >10K | | 728 | 2657 | |
| 17 | | >10K | | | 4619 | |
| 18 | | >10K | | 2 | 9 | NA: DP, EP1, EP3, FP, IP, TP |
| 19 | faster eluting diastereomer | 9288 | | 38 | 902 | |
| 20 | slower eluting diastereomer | 11 | 745 | 0.2 | 3 | EP3 (952), TP (5598) NA: DP, EP1, FP, IP |

-continued

| Entry | STRUCTURE | EP2 cAMP EC$_{50}$ (nM) | Ki (nM) | EP4 cAMP EC$_{50}$ (nM) | Ki EC$_{50}$ (nM) | OTHER RECEPTORS FLIPR EC$_{50}$ (nM) |
|---|---|---|---|---|---|---|
| 21 | faster eluting diastereomer | 76 | 2222 | 4 | 64 | NA: DP, EP1, EP3, FP, IP, TP |
| 22 | slower eluting diastereomer | 8 | 1034 | 0.3 | 4 | EP3 (4674) NA: DP, EP1, FP, IP, TP |
| 23 | faster eluting diastereomer |  | 9322 | 21 | 293 |  |
| 24 | slower eluting diastereomer | 30 | 1529 | 0.3 | 3 | EP3 (1512), TP (2446) NA: DP, EP1, FP, IP |
| 25 | faster eluting diastereomer | 164 | 3151 | 30 | 585 | NA: DP, EP1, EP3, FP, IP, TP |

| Entry | STRUCTURE | EP2 cAMP EC$_{50}$ (nM) | Ki (nM) | EP4 cAMP EC$_{50}$ (nM) | Ki EC$_{50}$ (nM) | OTHER RECEPTORS FLIPR EC$_{50}$ (nM) |
|---|---|---|---|---|---|---|
| 26 | *slower eluting diastereomer* | 8 | 1239 | 0.2 | 2 | EP3 (9946) NA: DP, EP1, FP, IP, TP |
| 27 | *faster eluting diastereomer* | 125 | 3632 | 18 | 457 | NA: DP, EP1, EP3, FP, IP, TP |
| 28 | *slower eluting diastereomer* | 10 | 1295 | 0.2 | 5 | EP3 (5989) NA: DP, EP1, FP, IP, TP |

Throughout this specification reference is made to publications such as US and foreign patent applications, journal articles, book chapters, and others. All such publications are expressly incorporated by reference in their entirety, including supplemental/supporting information sections published with the corresponding references, for all purposes unless otherwise indicated. To the extent that any recitations in the incorporated references conflict with any recitations herein, the recitations herein will control.

The foregoing description details specific methods and compositions that can be employed to make and use the compounds described herein, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the scope of the claims.

What is claimed is:

1. A compound represented by Formula 1:

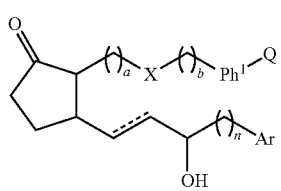

Formula 1 or a pharmaceutically acceptable salt thereof, wherein:
a dashed line indicates the presence or absence of a double bond;
Q is CO$_2$R$^1$, CH$_2$OR$^1$, CONR$^1$R$^2$, or optionally substituted tetrazol-5-yl, wherein R$^1$ and R$^2$ are independently H, C$_{1-6}$ alkyl, C$_{1-6}$ hydroxyalkyl, morpholinoethyl, or optionally substituted phenyl;
Ph$^1$ is optionally substituted interphenylene;
a and b are independently 0, 1, or 2;

X is CH₂, O, or S;
n is 0, 1, or 2; and
Ar is optionally substituted aryl or optionally substituted heteroaryl.

2. The compound of claim 1, wherein any substituents of Q, Ph¹, or Ar have a molecular weight of 15 g/mol to 500 g/mol.

3. The compound of claim 1, wherein Q is CO₂R¹.

4. The compound of claim 3, wherein R¹ is H or C₁₋₆ alkyl.

5. The compound of claim 1, wherein Ph¹ is optionally substituted p-interphenylene.

6. The compound of claim 5, wherein Ph¹ is unsubstituted p-interphenylene.

7. The compound of claim 1, wherein a is 1.

8. The compound of claim 1, wherein b is 0.

9. The compound of claim 1, wherein X is CH₂.

10. The compound of claim 1, wherein the dashed line represents a double bond.

11. The compound of claim 1, wherein n is 1.

12. The compound of claim 1, wherein Ar is optionally substituted phenyl.

13. The compound of claim 1, wherein Ar is optionally substituted 2,3-dihydrobenzo[b][1,4]dioxinyl.

14. The compound of claim 1, wherein Ar is optionally substituted benzothienyl.

15. The compound of claim 1, wherein Ar is optionally substituted naphthyl.

16. The compound of claim 1, wherein the compound is selected from the group consisting of:
   (E)-4-(2-(2-(3-hydroxy-4-(naphthalen-2-yl)but-1-en-1-yl)-5-oxocyclopentyl)ethyl)benzoic acid;
   (E)-4-(2-(2-(4-(3-chlorobenzo[b]thiophen-2-yl)-3-hydroxybut-1-en-1-yl)-5-oxocyclopentyl)ethyl)benzoic acid;
   (E)-4-(2-(2-(4-(3-fluorophenyl)-3-hydroxybut-1-en-1-yl)-5-oxocyclopentyl)ethyl)benzoic acid;
   (E)-4-(2-(2-(4-(3-chlorophenyl)-3-hydroxybut-1-en-1-yl)-5-oxocyclopentyl)ethyl)benzoic acid;
   (E)-4-(2-(2-(4-(3-bromophenyl)-3-hydroxybut-1-en-1-yl)-5-oxocyclopentyl)ethyl)benzoic acid;
   (E)-4-(2-(2-(3-hydroxy-4-(3-(trifluoromethyl)phenyl)but-1-en-1-yl)-5-oxocyclopentyl)ethyl)benzoic acid;
   (E)-4-(2-(2-(3-hydroxy-4-(7-methoxy-2,3-dihydrobenzo[b][1,4]dioxin-6-yl)but-1-en-1-yl)-5-oxocyclopentyl)ethyl)benzoic acid;
   (E)-4-(2-(2-(4-(benzo[b]thiophen-6-yl)-3-hydroxybut-1-en-1-yl)-5-oxocyclopentyl)ethyl)benzoic acid;
   (E)-4-(2-(2-(3-hydroxy-4-(6-methoxynaphthalen-2-yl)but-1-en-1-yl)-5-oxocyclopentyl)ethyl)benzoic acid;
   (E)-4-(2-(2-(3-hydroxy-4-(3-methoxynaphthalen-2-yl)but-1-en-1-yl)-5-oxocyclopentyl)ethyl)benzoic acid;
   (E)-4-(2-(2-(3-hydroxy-4-(7-methoxynaphthalen-2-yl)but-1-en-1-yl)-5-oxocyclopentyl)ethyl)benzoic acid;
   (E)-4-(2-(2-(4-(4-fluorophenyl)-3-hydroxybut-1-en-1-yl)-5-oxocyclopentyl)ethyl)benzoic acid;
   (E)-4-(2-(2-(4-(2-fluorophenyl)-3-hydroxybut-1-en-1-yl)-5-oxocyclopentyl)ethyl)benzoic acid;
   (E)-4-(2-(2-(4-(3,4-difluorophenyl)-3-hydroxybut-1-en-1-yl)-5-oxocyclopentyl)ethyl)benzoic acid;
   (E)-4-(2-(2-(4-(2,3-difluorophenyl)-3-hydroxybut-1-en-1-yl)-5-oxocyclopentyl)ethyl)benzoic acid; and
   (E)-4-(2-(2-(4-(2,5-difluorophenyl)-3-hydroxybut-1-en-1-yl)-5-oxocyclopentyl)ethyl)benzoic acid.

17. The compound of claim 1, wherein the compound is represented by a formula:

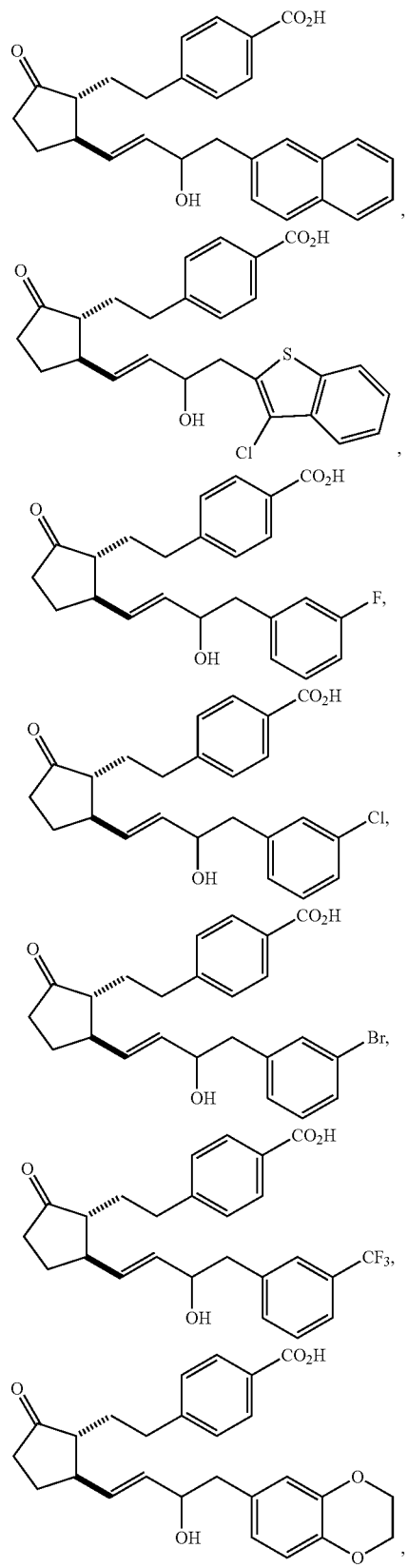

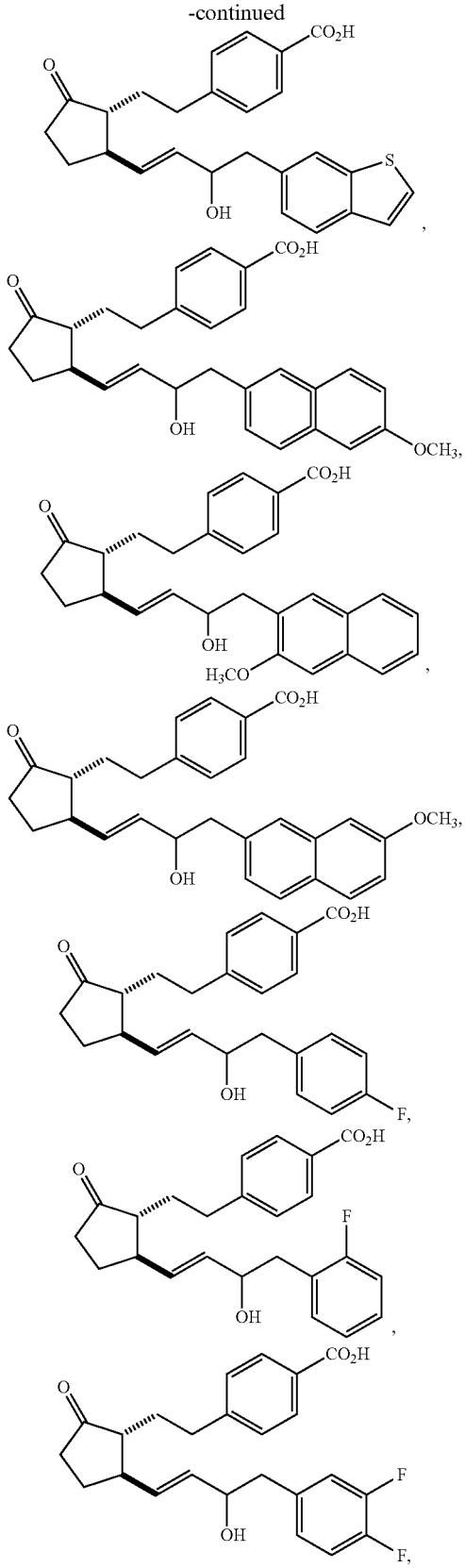

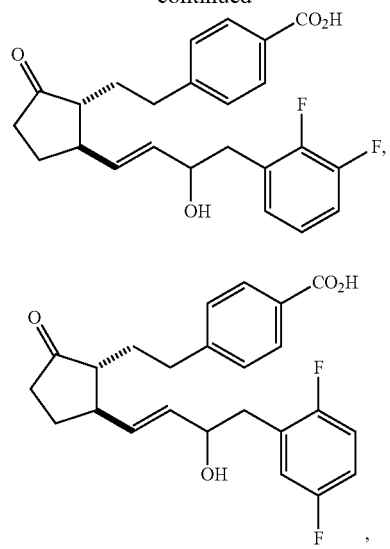

or a diastereomer thereof, or a pharmaceutically acceptable salt thereof.

18. The compound according to claim 1, wherein the compound binds to a prostaglandin receptor.

19. The compound according to claim 18, wherein the compound binds to a prostaglandin EP4 receptor with a binding $EC_{50}$ value of less than 200 nM.

20. The compound according to claim 18, wherein the compound is a prostaglandin receptor agonist.

21. The compound according to claim 20, wherein the compound is a prostaglandin EP4 receptor agonist with a functional $EC_{50}$ value of less than 1000 nM.

22. The compound according to claim 21, wherein the compound is more active at the prostaglandin EP4 receptor than at any other prostaglandin receptor.

23. An ophthalmic liquid comprising a compound according to claim 1, or a pharmaceutically acceptable salt thereof, and one or more pharmaceutically acceptable excipients.

24. A solid dosage form comprising a compound according to claim 1, or a pharmaceutically acceptable salt thereof, and one or more non-toxic solid carriers.

25. A method of reducing intraocular pressure comprising administering a compound according to claim 1, or a pharmaceutically acceptable salt thereof, to a mammal in need thereof.

26. A method of growing hair comprising administering a compound according to claim 1, or a pharmaceutically acceptable salt thereof, to a mammal in which hair growth is desirable.

27. A method of healing or mitigating a wound comprising administering a compound according to claim 1, or a pharmaceutically acceptable salt thereof, to a mammal in need thereof.

* * * * *